United States Patent
Bugni et al.

(10) Patent No.: US 11,028,113 B2
(45) Date of Patent: Jun. 8, 2021

(54) CYPHOMYCIN, COMPOSITIONS AND USES THEREOF

(71) Applicant: Wisconsin Alumni Research Foundation, Madison, WI (US)

(72) Inventors: Timothy S. Bugni, Madison, WI (US); Monica Tallarico Pupo, Ribeirão Preto (BR); David R. Andes, Madison, WI (US); Cameron R. Currie, Madison, WI (US); Humberto Enrique Ortega Dominguez, Ribeirão Preto (BR)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/664,722

(22) Filed: Oct. 25, 2019

(65) Prior Publication Data
US 2020/0131220 A1 Apr. 30, 2020

Related U.S. Application Data

(60) Provisional application No. 62/751,435, filed on Oct. 26, 2018.

(51) Int. Cl.
| | |
|---|---|
| *A61K 31/7048* | (2006.01) |
| *A61K 31/351* | (2006.01) |
| *A61K 31/4196* | (2006.01) |
| *A61K 31/4015* | (2006.01) |
| *A61K 31/513* | (2006.01) |
| *C07H 17/04* | (2006.01) |
| *C12N 1/20* | (2006.01) |

(52) U.S. Cl.
CPC .............. *C07H 17/04* (2013.01); *C12N 1/20* (2013.01); *A61K 31/351* (2013.01); *A61K 31/4015* (2013.01); *A61K 31/4196* (2013.01); *A61K 31/513* (2013.01); *A61K 31/7048* (2013.01)

(58) Field of Classification Search
CPC ......... C07H 17/00–08; A61K 31/7048; A61P 31/10
See application file for complete search history.

(56) References Cited

U.S. PATENT DOCUMENTS

2004/0180858 A1* 9/2004 Sommermeyer ....... C08B 35/06
514/60

FOREIGN PATENT DOCUMENTS

DE 4303513 A1 * 8/1994 ............. C07H 17/08

OTHER PUBLICATIONS

Gad, S., ed. Pharmaceutical Manufacturing Handbook, chapter 4, pp. 235-265. (Year: 2008).*

Takeuchi, T. et al "ATP depletion assay led to the isolation of new 36-membered polyol macrolides . . . " Org. Lett., vol. 19, pp. 4207-4210. (Year: 2017).*
Perez, M. et al "PM100117 and PM100118, new antitumor macrolides . . . " J. Antibiotics, pp. 1-7. (Year: 2015).*
Adnani, N. et al. Coculture of Marine Invertebrate-Associated Bacteria and Interdisciplinary Technologies Enable Biosynthesis and Discovery of a New Antibiotic, Keyicin. ACS Chem. Biol. 12, 3093-3102 (2017).
Andes, D. R. & Lepak, A. J. In vivo infection models in the pre-clinical pharmacokinetic/pharmacodynamic evaluation of antimicrobial agents. Curr. Opin. Pharmacol. 36, 94-99 (2017).
Arcamone, F. et al. Axenomycins. I. The Structure of Chromophore and Sugar moieties. Journal of the American Chemical Society. https://doi.org/10.1021/ja00787a048 (1973); b) Takahashi et al. Fungicidal GT35 manufacture with Streptomyces. Retrieved from http://www.sumobrain.com/patents/jp/New-substance-gt35-its-production/JPH09100290A.html (1997); c) Takeuchi, T. et al. ATP depletion assay led to the isolation of new 36-membered polyol macrolides Deplelides A and B from *Streptomyces* sp. MM581-NF1.
Arcamone, F., Barbieri, W., Franceschi, G., Penco, S., & Vigevani, A. (1973). Axenomycins. I. The Structure of Chromophore and Sugar moieties. Journal of the American Chemical Society. https://doi.org/10.1021/ja00787a048.
Baltz, R. H. Marcel Faber Roundtable: Is our antibiotic pipeline unproductive because of starvation, constipation or lack of inspiration? J. Ind. Microbiol. Biotechnol. 33, 507-513 (2006).
Bankevich, A. et al. SPAdes: A New Genome Assembly Algorithm and Its Applications to Single-Cell Sequencing. J. Comput. Biol. 19, 455-477 (2012).
Benjamini, Y. & Yekutieli, D. The control of the false discovery rate in multiple testing under dependency. Ann. Stat. 29, 1165-1188 (2001).
Blin, K. et al. antiSMASH 4.0—improvements in chemistry prediction and gene cluster boundary identification. Nucleic Acids Res. 1854, 1019-1037 (2017).
Blodgett, J. A. V. et al. Common biosynthetic origins for polycyclic tetramate macrolactams from phylogenetically diverse bacteria. Proc. Natl. Acad. Sci. 107, 11692-11697 (2010).
Book, A. J. et al. Evolution of high cellulolytic activity in symbiotic Streptomyces tnrougn selection of expanded gene content and coordinated gene expression. PLoS Biol. 14, 1-21 (2016).
Brown, E. D. & Wright, G. D. Antibacterial drug discovery in the resistance era. Nature 529, 336-343 (2016).
Carr, G. et al. Microtermolides A and B from termite-associated *Streptomyces* sp. and structural revision of vinylamycin. Org. Lett. 14, 2822-5 (2012).

(Continued)

*Primary Examiner* — Leigh C Maier
(74) *Attorney, Agent, or Firm* — Foley & Lardner LLP

(57) ABSTRACT

Cyphomycin, an isolated compound of Formula I or IA is provided. A compound isolated from insect *Streptomyces* and having a chemical formula of $C_{77}H_{122}O_{26}$ is also provided. Compositions including Cyphomycin, such as pharmaceutical compositions including effective amounts of Cyphomycin for treating fungal infections such as *Candida* and *Aspergillus*, including drug-resistant strains thereof, are also disclosed. Methods of treating fungal infections with Cyphomycin and compositions thereof are disclosed.

20 Claims, 15 Drawing Sheets

(56) References Cited

OTHER PUBLICATIONS

Chevrette, M. G. & Currie, C. R. Emerging evolutionary paradigms in antibiotic discovery. J. Ind. Microbiol. Biotechnol. (2018). doi:10.1007/s10295-018-2085-6.
Clardy, J., Fischbach, M. a. & Currie, C. R. The natural history of antibiotics. Curr. Biol. 19, 1-8 (2009).
Currie, C. R. et al. Ancient tripartite coevolution in the attine ant-microbe symbiosis. Science 299, 386-388 (2003).
Doroghazi, J. R. et al. A roadmap for natural product discovery based on large-scale genomics and metabolomics. Nat. Chem. Biol. 10, 963-968 (2014).
Eddy, S. R. Accelerated Profile HMM Searches. PLoS Comput. Biol. 7, e1002195 (2011).
Eisner, T. & Meinwald, J. Defensive secretions of arthropods. Science 153, 1341-50 (1966).
Fischbach, M. A. & Walsh, C. T. Antibiotics for emerging pathogens. Science 325, 1089-1093 (2009).
Fisher, M. C., Hawkins, N. J., Sanglard, D. & Gurr, S. J. Worldwide emergence of resistance to antifungal drugs challenges human health and food security. Science 360, 739-742 (2018).
Hanshew, A. S. et al. Characterization of Actinobacteria Associated with Three Ant-Plant Mutualisms. Microb. Ecol. 69, 192-203 (2015).
Hayakawa, M. & Nonomura, H. Humic acid-vitamin agar, a new medium for the selective isolation of soil actinomycetes. J. Ferment. Technol. 65, 501-509 (1987).
Helaly, S. E., Kulik, A., Zinecker, H., Ramachandaran, K., Tan, G. Y. A., Imhoff, J. F., . . . Sabaratnam, V. (2012). Langkolide, a 32-Membered Macrolactone Antibiotic Produced by Streptomyces sp. Acta 3062. Journal of Natural Products, 75(6), 1018-1024. https://doi.org/10.1021/np200580g.
Hug, J., Bader, C., Remškar, M., Cirnski, K. & M?ller, R. Concepts and Methods to Access Novel Antibiotics from Actinomycetes. Antibiotics 7, 44 (2018).
Hyatt, D. et al. Prodigal: prokaryotic gene recognition and translation initiation site identification. BMC Bioinformatics 11, 119 (2010).
Jang, K. H. et al. Anthracimycin, a Potent Anthrax Antibiotic from a Marine-Derived Actinomycete. Angew. Chemie Int. Ed. 52, 7822-7824 (2013).
Katoh, K. & Standley, D. M. Maffi Multiple Sequence Alignment Software Version 7: Improvements in Performance and Usability. Mol. Biol. Evol. 30, 772-780 (2013).
Kobayashi, Y., Tan, C.-H., & Kishi, Y. (2000). Toward Creation of a Universal NMR Database for Stereochemical Assignment: The Case of 1,3,5-Trisubstituted Acyclic Systems. Helvetica Chimica Acta, 83(9), 2562-2571. https://doi.org/10.1002/1522-2675(20000906)83:9<2562::AID-HLCA2562>3.0.CO;2-Z.
Kroiss, J. et al. Symbiotic streptomycetes provide antibiotic combination prophylaxis for wasp offspring. Nat. Chem. Biol. 6, 261-263 (2010).
Kumar, L. & Futschik, M. E. Mfuzz: A software package for soft clustering of microarray data. Bioinformation 2, 5-7 (2007).
Li, Q., Chen, X., Jiang, Y. & Jiang, C. Morphological Identification of Actinobacteria. in Actinobacteria—Basics and Biotechnological Applications (InTech, 2016). doi:10.5772/61461.
Ling, L. L. et al. A new antibiotic kills pathogens without detectable resistance. Nature 517, 455-459 (2015).
Liu, Y., Schroder, J. & Schmidt, B. Musket: a multistage k-mer spectrum-based error corrector for Illumina sequence data. Bioinformatics 29, 308-15 (2013).
Magoc, T. & Salzberg, S. L. FLASH: fast length adjustment of short reads to improve genome assemblies. Bioinformatics 27, 2957-63 (2011).
McDonald, B. R. & Currie, C. R. Lateral gene transfer dynamics in the ancient bacterial genus Streptomyces. MBio 8, e00644-17 (2017).
Medema, M. H. et al. Minimum Information about a Biosynthetic Gene cluster. Nat. Chem. Biol. 11, 625-631 (2015).
Medema, M. H., Cimermancic, P., Sali, A., Takano, E. & Fischbach, M. A. A systematic computational analysis of biosynthetic gene cluster evolution: lessons for engineering biosynthesis. PLoS Comput. Biol. 10, e1004016 (2014).
Miller, I., Chevrette, M. & Kwan, J. Interpreting microbial biosynthesis in the genomic age: biological and practical considerations. Mar. Drugs 15, 165 (2017).
Newman, D. J. & Cragg, G. M. Natural products as sources of new drugs from 1981 to 2014. J. Nat. Prod. 79, 629-661 (2016).
Oh, D. C., Poulsen, M., Currie, C. R. & Clardy, J. Sceliphrolactam, a polyene macrocyclic lactam from a wasp-associated Streptomyces sp. Org. Lett. 13, 752-755 (2011).
Oh, D.C., Poulsen, M., Currie, C. R. & Clardy, J. Dentigerumycin: a bacterial mediator of an ant-fungus symbiosis. Nat. Chem. Biol. 5, 391-393 (2009).
Payne, D. J. Microbiology. Desperately seeking new antibiotics. Science 321, 1644-5 (2008).
Perez, M. et al. PM100117 and PM100118, new antitumor macrolides produced by a marine Streptomyces caniferus GUA-06-05-006A. J. Antibiot. 69, 388-394 (2016).
Price, M. N., Dehal, P. S. & Arkin, A. P. FastTree 2—Approximately Maximum-Likelihood Trees for Large Alignments. PLoS One 5, e9490 (2010).
Pye, C. R., Bertin, M. J., Lokey, R. S., Gerwick, W. H. & Linington, R. G. Retrospective analysis of natural products provides insights for future discovery trends. Proc. Natl. Acad. Sci. 114, 5601-5606 (2017).
Schulze, C. J. et al. Genome-Directed Lead Discovery: Biosynthesis, Structure Elucidation, and Biological Evaluation of Two Families of Polyene Macrolactams against Trypanosoma brucei. ACS Chem. Biol. 150813113920008 (2015). doi:10.1021/acschembio.5b00308.
Scott, J. J. et al. Bacterial Protection of Beetle-Fungus Mutualism. Science 322, 63-63 (2008).
Smanski, M. J. et al. Synthetic biology to access and expand nature's chemical diversity. Nat. Rev. Microbiol. 14, 135-149 (2016).
Sprenger, M. & Fukuda, K. New mechanisms, new worries. Science 351, 1263-1264 (2016).
Stamatakis, A. RAxML version 8: A tool for phylogenetic analysis and post-analysis of large phylogenies. Bioinformatics 30, 1312-1313 (2014).
Stork, N. E., McBroom, J., Gely, C. & Hamilton, A. J. New approaches narrow global species estimates for beetles, insects, and terrestrial arthropods. Proc. Natl. Acad. Sci. 112, 7519-23 (2015).
Takahashi, Isami; Seike, Yasushi; Uosaki, Yoichi; Ochiai, K. (1997). Fungicidal GT35 manufacture with Streptomyces. Retrieved from http://www.sumobrain.com/patents/jp/New-substance-gt35-its-production/JPH09100290A.html.
Udwary, D. W. et al. Genome sequencing reveals complex secondary metabolome in the marine actinomycete Salinispora tropica. Proc. Natl. Acad. Sci. 104, 10376-10381 (2007).
VanArnam, E. B. et al. Selvamicin, an atypical antifungal polyene from two alternative genomic contexts. Proc. Natl. Acad. Sci. 113, 12940-12945 (2016).
Yoshihisa Kobayashi, Jinhwa Lee, Kenichi Tezuka, and, & Kishi*, Y. (1999). Toward Creation of a Universal NMR Database for the Stereochemical Assignment of Acyclic Compounds:? The Case of Two Contiguous Propionate Units. https://doi.org/10.1021/OL9903786.
Zhao, M. et al. In Vivo Pharmacokinetics and Pharmacodynamics of APX001 against Candida spp. in a Neutropenic Disseminated Candidiasis Mouse Model. Antimicrob. Agents Chemother. 62, e02542-17 (2018).
Zhao, M., Lepak, A. J. & Andes, D. R. Animal models in the pharmacokinetic / pharmacodynamic evaluation of antimicrobial agents. Bioorg. Med. Chem. 24, 6390-6400 (2016).
Ziemert, N. et al. Diversity and evolution of secondary metabolism in the marine actinomycete genus Salinispora. Proc. Natl. Acad. Sci. 111, E1130-9 (2014).
Zipperer, A. et al. Human commensals producing a novel antibiotic impair pathogen colonization. Nature 535, 511-6 (2016).

* cited by examiner

CYPHOMYCIN, COMPOSITIONS AND USES THEREOF

CROSS-REFERENCE TO RELATED PATENT APPLICATIONS

This application claims the benefit of priority to U.S. Provisional Application No. 62/751,435, filed on Oct. 26, 2018, and which is incorporated herein by reference in its entirety for all purposes.

STATEMENT OF GOVERNMENT SUPPORT

This invention was made with government support under TW009872 and AI109673 awarded by the National Institutes of Health. The government has certain rights in the invention.

FIELD OF THE TECHNOLOGY

The present technology relates to a new compound called cyphomycin, compositions and methods of use thereof. The new isolated compound and compositions containing it are useful as antifungals, and show activity even against multi-drug resistant fungal infections.

SUMMARY

A new compound, called cyphomycin has been discovered and isolated from *Streptomyces*, a bacterium collected from *Cyphormex*, a species of fungus-growing ant. Cyphomycin has the chemical formula $C_{77}H_{122}O_{26}$. Isolated cyphomycin exhibits one or more of the following spectral features: one or more $^{13}C$ NMR peaks at or about the chemical shifts shown in Table 2 herein; one or more $^{1}H$ NMR peaks at or about the chemical shifts shown in Table 2; or one or more UV $\lambda_{max}$ at about 204, about 248, about 254, or about 334 nm. Isolated cyphomycin has the structure of Formula I:

Formula I

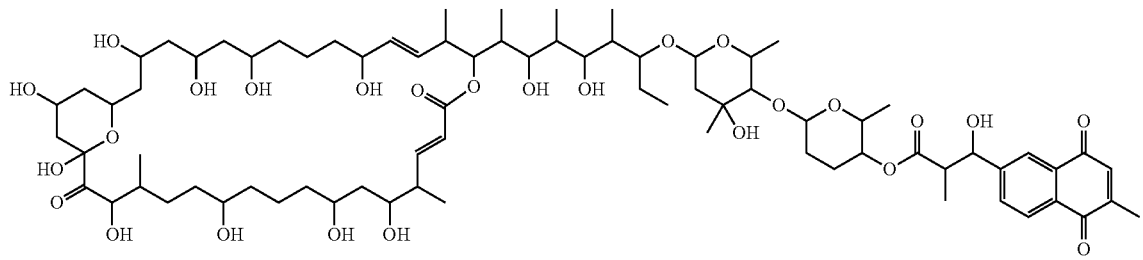

Pharmaceutical compositions including cyphomycin and a pharmaceutically acceptable carrier are also provided. Methods of treating fungal infections by administering an effective amount of cyphomycin to a mammal in need thereof are disclosed.

The foregoing summary is illustrative only and is not intended to be in any way limiting. In addition to the illustrative aspects, embodiments, and features described above, further aspects, embodiments, and features will become apparent by reference to the drawings and the following detailed description.

Figure 16:
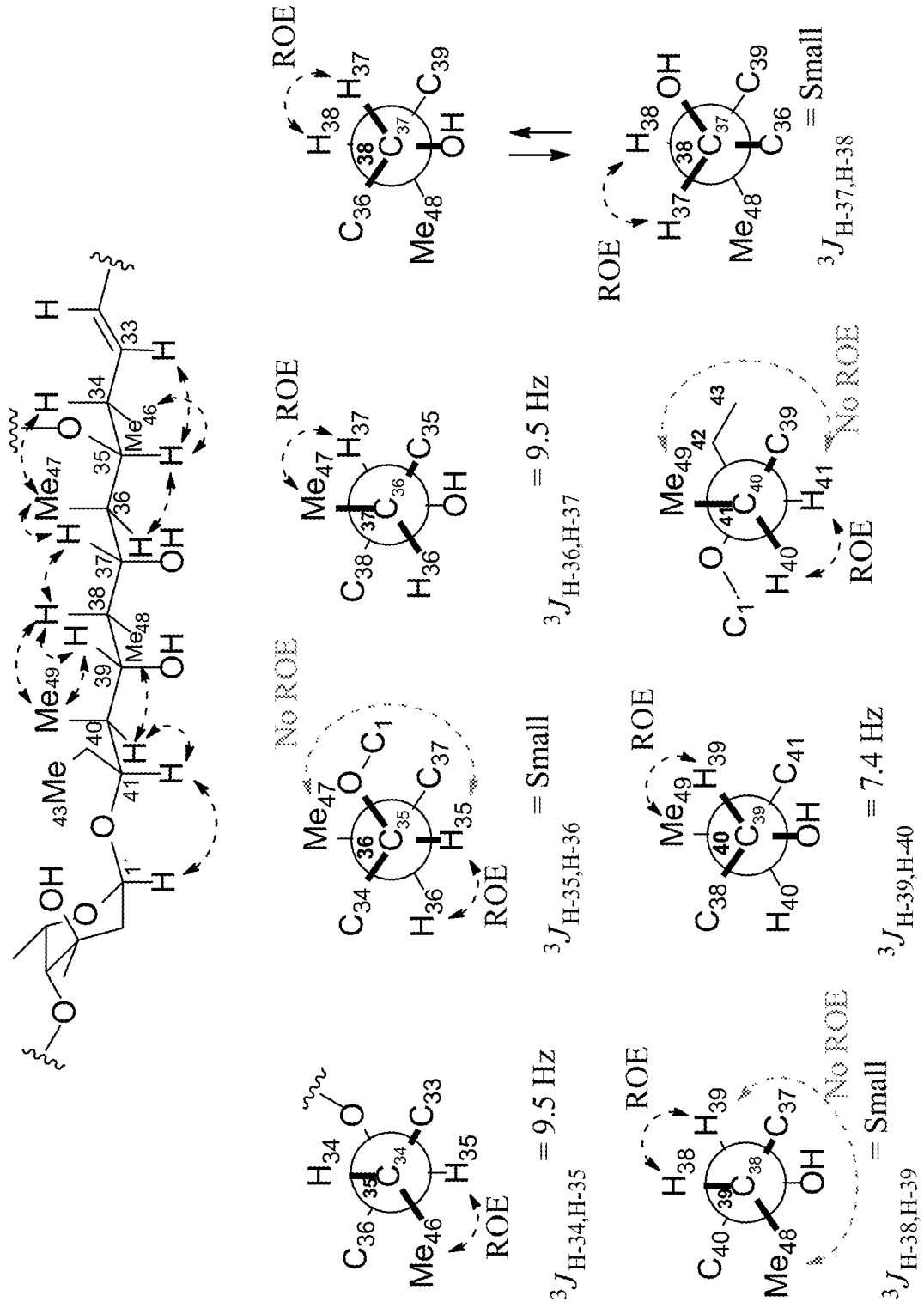

FIG. 16 shows relative configuration proposed for fragment of C-32 to C-43.

DETAILED DESCRIPTION

The present technology provides an isolated compound useful for the treatment of fungal infections, including multi-drug resistant fungal infections. Thus, in accordance with one aspect, the technology includes a compound isolated from *Streptomyces* associated *Cyphormex*, a fungus-growing ant species. The compound, called cyphomycin, represents a new class of antifungal compounds and in any embodiment of the present technology, has the structure shown by Formula I:

Formula I

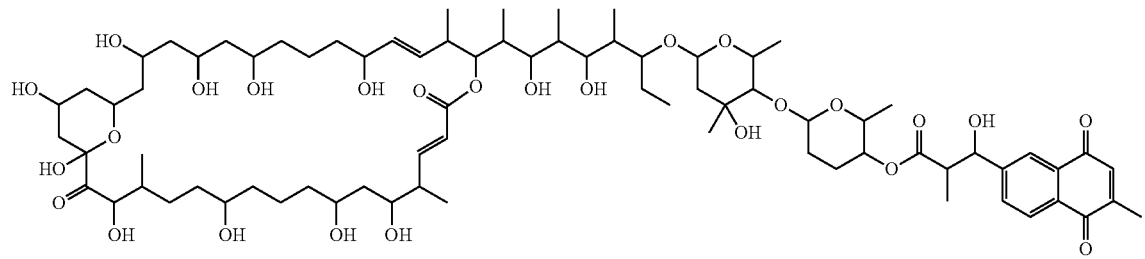

Isolated cyphomycin has a chemical formula of $C_{77}H_{122}O_{26}$ and exhibits any of the $^{13}C$ NMR peaks at or about the chemical shifts shown in Table 2, including 1, 2, 3, 4, 5, 6, 7, 8, 9, 10 or more thereof. For example, cyphomycin may exhibit 1, 2, 3, 4, 5, 6, 7, 8, 9, or 10 $^{13}C$ NMR peaks including those at about 210.6, about 168.7, about 122.1, about 153.5, about 135.2, about 133.1, about 175.5, about 150.3, about 186.2, and about 186.3 ppm. Similarly, isolated cyphomycin exhibits any of the $^1H$ NMR peaks at or about the chemical shifts shown in Table 2, including 1, 2, 3, 4, 5, 6, 7, 8, 9, 10 or more thereof. For example, cyphomycin may exhibit 1, 2, 3, 4, 5, 6, 7, 8, 9, or 10 $^1H$ NMR peaks selected from those at about 8.07, about 8.01, about 7.79, about 7.06, about 6.88, about 5.86, about 5.53, about 5.49, about 5.14, about 4.69, and about 3.54 ppm. Cyphomycin may exhibit one, two, three or four UV absorptions ($\lambda_{max}$) selected from those at about 204, about 248, about 254, and about 334 nm. The term "about" will be understood by those of skill in the art to include values within ±2% of the stated value, or in some embodiments, ±1% or even ±0.5% of the stated values.

In any embodiment described herein, a compound of Formula I may be the diastereomer shown below (Formula IA). The numbering of the compound is as indicated below, and such numbering is referred to herein.

meric or geometric isomeric forms, it should be understood that the technology encompasses any tautomeric, conformational isomeric, stereoisomeric and/or geometric isomeric forms of the compounds having one or more of the utilities described herein, as well as mixtures of these various different forms.

Stereoisomers of compounds (also known as optical isomers) include all chiral, diastereomeric, and racemic forms of a structure, unless the specific stereochemistry is expressly indicated. Thus, compounds disclosed herein include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

In another aspect the present technology provides a pharmaceutical composition including cyphomycin as described herein and a pharmaceutically acceptable carrier. The pharmaceutical compositions of any embodiment herein may be formulated for oral, parenteral, nasal, topical administration or any of the routes discussed herein. In any embodiment herein, the pharmaceutical composition may include an effective amount of a compound of any embodiment of the Formula IA

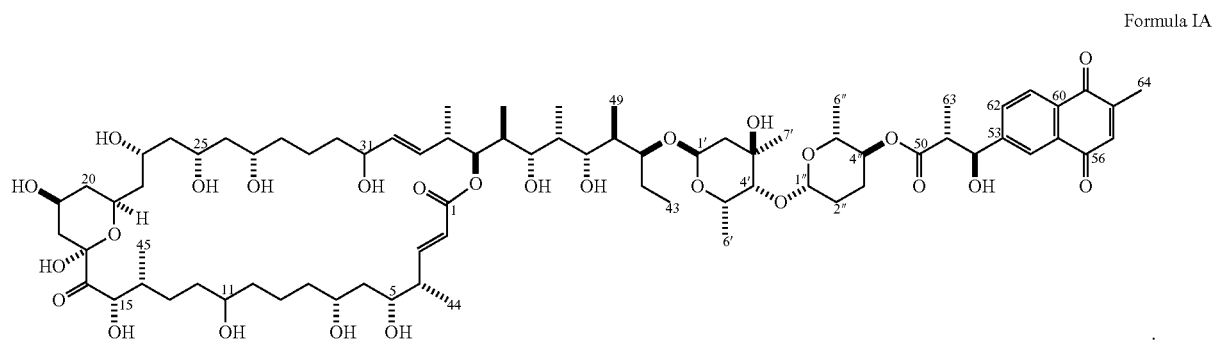

The compounds described herein may be isolated at various purities, e.g., a purity of at least 60 wt %, at least 70 wt %, at least 80 wt %, at least 90 wt %, at least 95 wt %, at least 96, at least 97 wt %, at least 98 wt %, at least 99 wt % or at least 99.5 wt %.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereoisopresent technology. The effective amount may be an effective amount for treating a fungal infection, including those caused by any of the fungi disclosed herein. In any embodiments, the effective amount of compound may be an effective amount for treating any infection due to drug-resistant fungi, including those disclosed herein (see below).

The present technology provides methods of treating a fungal infection comprising administering an effective amount of cyphomycin, or a pharmaceutical composition as described herein to a mammal in need thereof. The mammal may be, e.g., a human, primate (e.g. monkey, chimpanzee, ape), cat, dog, pig, mouse, rat, horse, sheep, among others. In any embodiment described herein, the mammal may be human. The infection may occur, e.g., in the skin, mouth, pharynx, esophagus, toenails, fingernails, urogenital tract, or lungs, or may be systemic, in, e.g., immunocompromised patients. In any embodiment of the present methods, the fungal infection may be caused by one or both of *Candida* or *Aspergillus*. In any embodiments of the present methods, the fungal infection may be caused by *Aspergillus*, such as *Aspergillus fumigatus*, or it may be caused by *Candida*, e.g., *Candida albicans, Candida auris, Candida enolase, Candida tropicalis, Candida glabrata, Candida krusei, Candida parapsilosis, Candida stellatoidea, Candida parakawsei, Candida lusitaniae, Candida pseudotropicalis*, and *Candida guilliermondi*. In any embodiment described herein, the fungal infection may be caused by one or more of drug-resistant fungi, such as, but not limited to, *Aspergillus fumigatus* (e.g., 11628), *Candidas albicans, Candida glabrata* (e.g., 4720), *Candida auris* (e.g., B11211). Similarly, the compounds and compositions described herein may be used for therapy, such as for treatment of fungal infections such as any of those described herein, or for use in the manufacture of a medicament for any such treatments.

In another aspect, the present technology provides pharmaceutical compositions of cyphomycin with a second antifungal agent (or combination of agents) different from cyphomycin, including but not limited to azoles, echinocandins, or polyenes, as well as methods of using the same. Antifungal agents include drugs which demonstrate clinical benefit in treatment of fungal infections in a mammal, including a human. Suitable second antifungal agents include but are not limited to one or more of amphotericin B, flucytosine, fluconazole, micafungin, and forazoline. In any embodiment described herein, an effective amount of a compound as described herein (e.g., cyphomycin), a salt thereof or a pharmaceutical composition comprising the compound and a pharmaceutically acceptable carrier, may be administered to a mammal in need thereof, wherein the second antifungal agent(s) is/are administered to the mammal in need thereof simultaneously, sequentially or separately with a compound as described herein, or any embodiment of the pharmaceutical composition as describe herein.

"Treating" within the context of the instant technology, means alleviation, in whole or in part, of symptoms associated with a disorder or disease, or slowing, inhibition or halting of further progression or worsening of those symptoms, or prevention or prophylaxis of the disease or disorder in a subject at risk for developing the disease or disorder. For example, within the context of treating fungal infections, successful treatment may include reduction or eradication of the pathogenic fungus, from the body; clinical benefit; an alleviation of symptoms, such as a reduction or elimination of rash, itching, chafing, burning, throat thrush, redness, soreness, fever, cough, night sweats, weight loss, wheezing, and shortness of breath.

As used herein, an "effective amount" of a compound of the present technology refers to an amount of the compound that alleviates, in whole or in part, symptoms associated with a disorder or disease, or slows or halts of further progression or worsening of those symptoms, or prevents or provides prophylaxis for the disease or disorder in a subject at risk for developing the disease or disorder. Those skilled in the art are readily able to determine an effective amount. For example, one way of assessing an effective amount for a particular disease state is by simply administering a compound of the present technology to a patient in increasing amounts until progression of the disease state is decreased or stopped or reversed. An "effective amount" of a compound of the present technology also refers to an amount of the compound that, for example, reduces a population of fungi where the fungal population may be outside a subject (e.g., in a media in a container).

The instant technology also provides for compositions and medicaments including a compound disclosed herein and a pharmaceutically acceptable carrier. Such compositions may be prepared by mixing one or more compounds of the present technology, pharmaceutically acceptable salts thereof or stereoisomers thereof, with pharmaceutically acceptable carriers, excipients, binders, diluents or the like to treat fungal infections. The compounds and compositions of the present technology may be used to prepare formulations and medicaments that treat a variety of fungal infections, e.g., *Candida* and *Aspergillus* as disclosed herein. Such compositions can be in the form of, for example, granules, powders, tablets, capsules, creams, ointments, syrup, suppositories, injections, emulsions, elixirs, suspensions or solutions. The instant compositions can be formulated for various routes of administration, for example, by oral, parenteral, topical, injection, rectal, nasal, vaginal, or via implanted reservoir. Parenteral or systemic administration includes, but is not limited to, subcutaneous, intravenous, intraperitoneally, intramuscular, intrathecal, intracranial, and intracerebroventricular injections. The following dosage forms are given by way of example and should not be construed as limiting the instant technology.

For oral, buccal, and sublingual administration, powders, suspensions, granules, tablets, pills, capsules, gelcaps, and caplets are acceptable as solid dosage forms. These can be prepared, for example, by mixing one or more compounds disclosed herein, or pharmaceutically acceptable salts or stereoisomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions, which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di-, or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology also may be formulated as a composition for topical administration (e.g., vaginal cream). These formulations may contain various excipients known to those skilled in the art. Suitable excipients may include, but are not limited to, cetyl esters wax, cetyl alcohol, white wax, glyceryl monostearate, propylene glycol monostearate, methyl stearate, benzyl alcohol, sodium lauryl sulfate, glycerin, mineral oil, water, carbomer, ethyl alcohol, acrylate adhesives, polyisobutylene adhesives, and silicone adhesives.

The composition may be in the form of a vaginal cream containing the composition of matter as set forth herein present in a nonliquefying base. The nonliquefying base may contain various inactive ingredients such as, for example, cetyl esters wax, cetyl alcohol, white wax, glyceryl monostearate, propylene glycol monostearate, methyl stearate, benzyl alcohol, sodium lauryl sulfate, glycerin, and mineral oil. Such composition may be formulated similar to PREMARIN® Vaginal Cream made commercially available by Wyeth-Ayerst Laboratories.

Dosage units for rectal administration may be prepared in the form of suppositories which may contain the composition of matter in a mixture with a neutral fat base, or they may be prepared in the form of gelatin-rectal capsules which contain the active substance in a mixture with a vegetable oil or paraffin oil.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. Formulations for inhalation administration contain as excipients, for example, lactose, polyoxyethylene-9-lauryl ether, glycocholate and deoxycholate. Aqueous and nonaqueous aerosols are typically used for delivery of inventive compounds by inhalation.

Ordinarily, an aqueous aerosol is made by formulating an aqueous solution or suspension of the compound together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins such as serum albumin, sorbitan esters, oleic acid, lecithin, amino acids such as glycine, buffers, salts, sugars or sugar alcohols. Aerosols generally are prepared from isotonic solutions. A nonaqueous suspension (e.g., in a fluorocarbon propellant) can also be used to deliver compounds of the present technology.

Aerosols containing compounds for use according to the present technology are conveniently delivered using an inhaler, atomizer, pressurized pack or a nebulizer and a suitable propellant, e.g., without limitation, pressurized dichlorodifluoromethane, trichlorofluoromethane, dichlorotetrafluoroethane, nitrogen, air, or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch. Delivery of aerosols of the present technology using sonic nebulizers is advantageous because nebulizers minimize exposure of the agent to shear, which can result in degradation of the compound.

For nasal administration, the pharmaceutical formulations and medicaments may be a spray, nasal drops or aerosol containing an appropriate solvent(s) and optionally other compounds such as, but not limited to, stabilizers, antimicrobial agents, antioxidants, pH modifiers, surfactants, bioavailability modifiers and combinations of these. For administration in the form of nasal drops, the compounds may be formulated in oily solutions or as a gel. For administration of nasal aerosol, any suitable propellant may be used including compressed air, nitrogen, carbon dioxide, or a hydrocarbon based low boiling solvent.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant technology.

A therapeutically effective amount of a compound of the present technology may vary depending upon the route of administration and dosage form. Effective amounts of such compounds typically fall in the range of about 0.01 up to about 100 mg/kg/day, about 0.01 to about 75 mg/kg/day, about 0.05 to about 50 mg/kg/day, about 0.01 to about 25 mg/kg/day, about 0.01 to about 15 mg/kg/day, about 0.01 to about 10 mg/kg/day, and more typically in the range of about 0.1 up to 5 mg/kg/day, about 0.1 up to 4 mg/kg/day, about 0.1 up to 3 mg/kg/day, about 0.1 up to 2 mg/kg/day, about 0.1 up to 1 mg/kg/day, about 0.2 up to 5 mg/kg/day, about 0.5 up to 5 mg/kg/day, about 1 up to 5 mg/kg/day, about 1.5 up to 5 mg/kg/day, or about 2 up to 5 mg/kg/day. Typically, the compound or compounds of the instant technology are selected to provide a formulation that exhibits a high therapeutic index. The therapeutic index is the dose ratio between toxic and therapeutic effects and can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology is further illustrated by the following examples, which should not be construed as limiting in any way.

EXAMPLES

Example 1: Isolation of *Streptomyces* From Insects and Other Sources

Biological Material. Host-associated strains were obtained from seven field collections (Florida, Hawaii, Alaska, New Mexico, Wisconsin, California, Brazil) from 2014-2016, with various Currie lab archival strains. Each host was collected using sterile forceps and deposited into a pre-sterilized, pre-barcoded container. Field collections focused heavily on insects that were not in direct contact with soil to avoid the possibility of soil contamination in subsequent surface isolation. Metadata recorded at each field site included: researcher information, date, location, GPS coordinates, micro and macro environment, host description, as well as photographs of each field-site. All specimens were assigned a unique host-identification number (HID) and stored at 4° C.

Processing and Bacterial Isolation. All hosts are photographed via dissecting scope and cataloged by HID. Insect specimens were processed based on host integrity. If the sample was large enough and completely intact it was processed for external and internal microbial isolates. Large samples were also processed by particle method, using a sterilized surgical scalpel to remove portions of each specimen and placing each piece on an agar plate. If small, degraded or compromised, samples were processed using a combination method: the same procedure as the internal isolation without surface sterilization. External isolation involves transferring host specimen into a 1.5 mL microcentrifuge tube, adding 125*x (x=number of plates) μL phosphate-buffered saline (PBS), vortexing gently at 50% speed for 10 seconds, and transferring 100 μL to various media. To select for Actinobacteria, humic acid Agar (HV)[42] and selective chitin media[43] with 20 mL/1 L nystatin, and 10 mL/1 L cycloheximide added to select against fungal isolates were used. After plating for external isolates, a sterilization wash is preformed to isolate internal microbes. The same microcentrifuge tube from the external was filled with 1 mL of 70% ethanol and gently mixed by inversion for 1 minute. Ethanol waste was removed and 1 mL of 1% bleach with 0.1% tween20 solution was added and mixed gently for 30 seconds by inversion. Supernatant was removed and host specimen was rinsed 3× using 1 mL PBS buffer for 10 seconds. After external sterilization, 125*x (x=number of plates) μL of PBS was added to the tube. The specimen was then ground-up using a sterile pestle inside the tube. Using a wide bore 200 μL tip, 100 μL of slurry was transferred onto a pre-labeled media plate (HV & chitin) and spread evenly. The last 100 μL was pipetted into a DNA voucher containing 900 uL of 95% ethanol for storage.

Bacterial Isolation. HV and chitin isolation plates were incubated aerobically at room temperature (28° C.) and checked for bacterial growth at 14 d, 30 d and 90 d. Colonies exhibiting characteristic Actinobacterial morphology[44] were assigned a strain identification number before isolation onto fresh HV or chitin media and incubation at 28° C.

A large number (1,162) of *Streptomyces* strains from insects were identified using the above techniques and were screened as described in Example 2, including ISID, the *Streptomyces* strain that produces cyphomycin.

Example 2: Screening of Isolates for Antimicrobial Activity

Inhibition Bioassays & Scoring. Isolates were inoculated along the center of wells. Each well contained 3 mL of yeast peptone mannitol (YPM) agar (2 g yeast extract, 2 g peptone, 4 g mannitol, 15 g agar, 1 L $H_2O$). Actinobacteria were incubated at 28° C. for 5 d prior to the addition of the test pathogens. For fungal pathogens, spore stocks of each fungal strain were diluted 1:10. Cultures were shaken overnight at 28° C. and diluted 1:10. Diluted cultures were used to inoculate 3 μl in the center of the well and the non-pathogen controls. Plates were maintained at 28° C. for 7 d. Inhibition was scored in binary, as 0 (no inhibition) or 1 (inhibition). For a subset of isolates, experimental wells were assigned a rating from 0-3 depending on the level of inhibition (0—no inhibition, 1—slight inhibition, 2—presence of a zone of inhibition, 3—complete inhibition). Inhibition fraction was determined by taking the average inhibition of Strain X vs. Pathogen Y to account for variance if multiple X by Y challenges were run. This was done for all pathogens against X. Fungal averages were then computed to find the inhibition fraction for X. Strains were grouped by source and p-values were calculated by T-test with Benjamini/Yekutieli correction[47]. Fuzzy clustering was used to group inhibitory profiles using Mfuzz[48].

Figure 1:
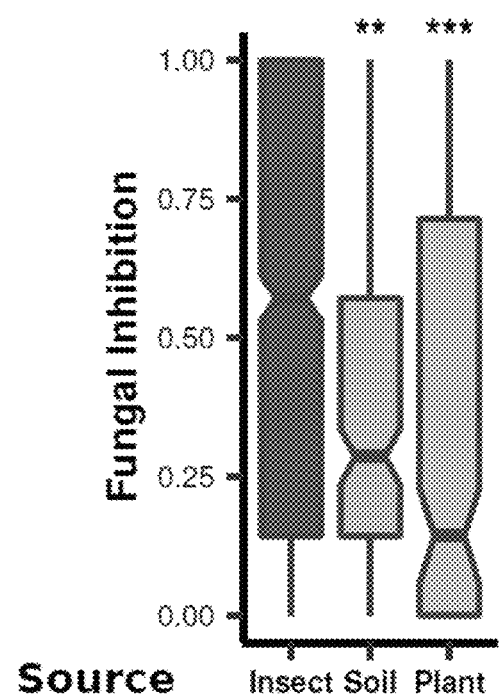
FIG. 1 shows a graph summarizing inhibition of fungal pathogens by insect-associated *Streptomyces* isolates compared to soil and plant-based *Streptomyces* isolates.

Using this general procedure, a panel of 27 clinically and/or ecologically relevant microbes were tested against the *Streptomyces* strains identified in Example 1, and hit rates compared to strains isolated from soil and plants. Fungal pathogens are significantly more inhibited by insect-associated isolates compared to soil- and plant-sourced *Streptomyces* (see FIG. 1).

Example 3: Characterizing Anti-Microbial Activity of Isolates

Figure 2:
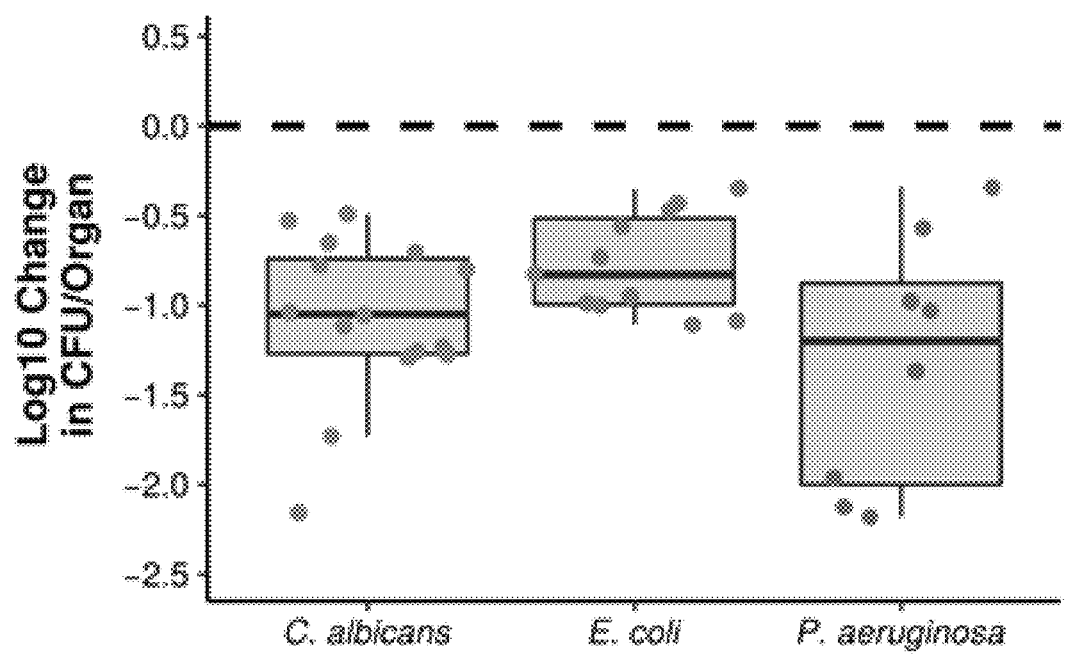
FIG. 2 shows a summary graph of antimicrobial activity of fractionated extracts from insect microbiomes are active in multiple murine models of drug-resistant infection, including *C. albicans*, *E. coli*, and *P. aeruginosa*.

Mouse studies. All mouse experiments and protocols approved by the University of Wisconsin Institutional Animal Care and Use Committee. Results are shown in FIG. 2.

*Candida* model. Six-week-old, specific-pathogen-free, female ICR/Swiss mice weighing 23 to 27 g were used for all studies (Harlan Sprague-Dawley, Indianapolis, Ind.). Animals were maintained in accordance with the criteria of the Association for Assessment and Accreditation of Laboratory Animal Care. All animal studies were approved by the Animal Research Committee of the William S. Middleton Memorial Veterans Hospital. Mice were rendered neutropenic (neutrophils, 100/mm3) by injection with cyclophosphamide (Mead Johnson Pharmaceuticals, Evansville, Ind.) subcutaneously 4 days (150 mg/kg) and 1 day (100 mg/kg) before infection and 2 days after infection (100 mg/kg). Previous studies have shown neutropenia (neutrophils, 100/mm$^3$) in this model for the 96-h study period[38]. Organisms were subcultured on SDA 24 h prior to infection. Inoculum was prepared by placing three to five colonies into 5 ml of sterile pyrogen-free 0.9% saline warmed to 35° C. The final inoculum was adjusted to a 0.6 transmittance at 530 nm. Fungal counts of the inoculum determined by viable counts of *C. albicans* on SDA were 6.29 0.03, 6.15 0.10, and 6.30 0.07 log10 CFU/ml, respectively. Disseminated infection with the *Candida* was achieved by injection of 0.1 ml of inoculum via the lateral tail vein 2 h prior to the start of drug therapy. Treatment period was 8 h. Animals were sacrificed by CO2 asphyxiation. Kidneys of each mouse were removed and placed in sterile 0.9% saline at 4° C. The homogenate was serially diluted and aliquots were plated on SDA for viable fungal colony counts after incubation for 24 h at 35° C. The lower limit of detection was 100 CFU/ml. Results were expressed as the mean number of CFU per kidney for three mice. No-treatment and zero-hour controls were included in all experiments.

In vivo murine studies. Mice were treated 2 h after infection and sampled 6-8 h after treatment. Bacteria were grown in three different media (A media, ISP-2, YPM, and A-Medium; 100 mL each) with Diaion HP20 (7% by weight) and shaken at 200 rpm at 28° C. for seven days. Filtered HP20 was washed with water and extracted with acetone. The acetone extracts from the three media were combined and followed by solid phase extraction using ENV$^+$ columns to generation four fractions. These four fractions were further purified by HPLC to generate 80 fractions for each strain in a 96-well plate. High throughput screening was used to evaluate the antimicrobial activity of these fractions. Dereplication based on 1.7 mm NMR and HRMS was used to select promising hits. Select strains were re-grown in the large scale in the three media, and followed the same process mentioned before to generate the fractions containing potential novel active compounds. These fractions were formulated and tested in vivo activity.

In vitro MIC susceptibility testing. MICs of Cyphomycin for the *Candida* isolates were determined using a broth microdilution method in accordance with the guidelines presented in Clinical and Laboratory Standards Institute (CLSI) document M27-A3 for *Candida* and M38-A2 for *Aspergillus*[36,38]. MIC values of cyphomycin were defined as the lowest concentration at which a prominent decrease in growth turbidity (i.e., 50% reduction in growth determined spectrophotometrically) relative to the turbidity of the compound-free control at 600 nm was observed. Median MIC from replicate assays is reported. Results are shown in Table 1 for cyphomycin activity against drug-resistant fungi.

TABLE 1

| Strain | Drug Resistance Phenotype | Cyphomycin MIC (ug/mL) |
| --- | --- | --- |
| *Aspergillus fumigatus* 11628 | Triazole | 0.5 |
| *Candida glabrata* 4720 | Echinocandin | 0.5 |
| *Candida auris* B11211 | Amphotericin B | 4 |

Example 4: Toxicity of Insect-Associated *Streptomyces* Antimicrobials

Hemolysis assay. Assays were performed in 384 well plates using sheep blood (0.1% triton as the positive control). Sheep's blood (Ward's Science) was washed with PBS and diluted to a concentration of 6×10^7 red blood cells per mL. 50 µL of blood was incubated with a test compound or fraction for 1 hour, and subsequently pelleted at 4000 rpm for 10 minutes. 30 µL supernatant was transferred to a clear plate and OD570 was read. An increase in OD indicated the red blood cell lysis and hemolytic activity.

Figure 3:
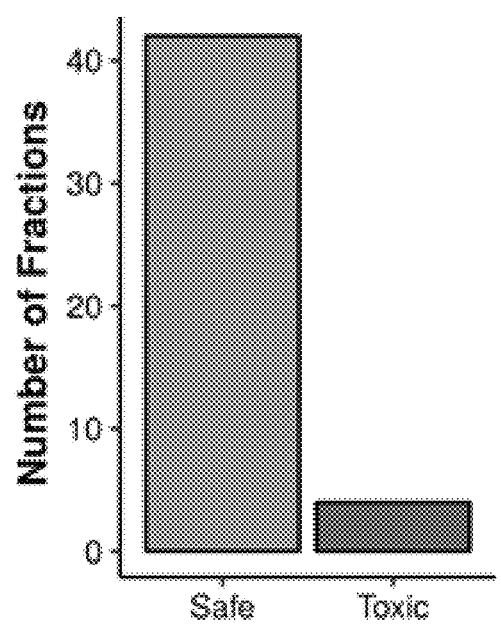
FIG. 3 shows a summary graph of a hemolysis assay performed to assess toxicity of fractions from insect microbiome *Streptomyces*.

A compound or fraction was deemed "safe" if it showed no toxicity in the hemolysis assay at >100× the concentration associated with efficacy. As shown in FIG. 3, 91% of fractions from insect microbiome *Streptomyces* show no toxicity in hemolysis assays.

Example 5—Cyphomycin Culturing and Isolation

*Streptomyces* ISID311 was grown in A-medium broth (20 g soluble starch, 10 g glucose, 5 g peptone, 5 g yeast extract, 5 g $CaCO_3$ per liter) using Fernbach flasks [5×(1 L of medium in 2.8 L+70 g of HP20)] and shaken for 7 days at 28° C. and 200 rpm. The HP20 was filtered and washed with distillated water and soaked with acetone. Organic solvent was filtered, vacuum dried, and partitioned with ethyl acetate/water. Organic phase was separated and dried to give the crude extract (2.3044 g). Extract was purified by SPE-C18 (55 µm, 20 g) using the following gradient: 200 mL (20% MeOH—$H_2O$, A1: 72.8 mg); 200 mL (40% MeOH—$H_2O$, A2: 152.5 mg); 200 mL (60% MeOH—$H_2O$, A3: 132.3 mg); and 200 mL (100% MeOH, A4: 1.9349 g).

A4 was purified by semi-preparative HPLC using C18 semipreparative column (Phenomenex Luna, $C_{18}$(2), 5 µm, 250×10 mm) and the following gradient of MeOH and $H_2O$ (containing 0.1% of acetic acid) at 4 mL/min: min 1-20 (linear gradient from 80% MeOH—$H_2O$ to 100% MeOH); min 20-22 (isocratic flow of 100% MeOH); min 22-22.5 (linear gradient from 100% MeOH to 80% MeOH—$H_2O$); and min 22.5-27.5 (isocratic flow of 80% MeOH—$H_2O$) to yield cyphomycin (89.0 mg, $t_R$=11.4 min).

Example 6: Cyphomycin Structure Elucidation

Analytical data were gathered for cyphomycin, including optical rotation, UV, HRMS, and NMR spectra.

Cyphomycin: yellow amorphous solid; $[\alpha]_D^{26}$ =+25.5 (c 0.15, MeOH); UV (MeOH) $\lambda_{max}$ (log ε) 204 (5.2), 248 (5.0), 254 (5.0), 334 (4.2). The molecular formula of cyphomycin is $C_{77}H_{122}O_{26}$ based on positive ion HRESIMS ([M+H]$^+$ m/z 1463.8282, err 1.0 ppm).

Figure 4:
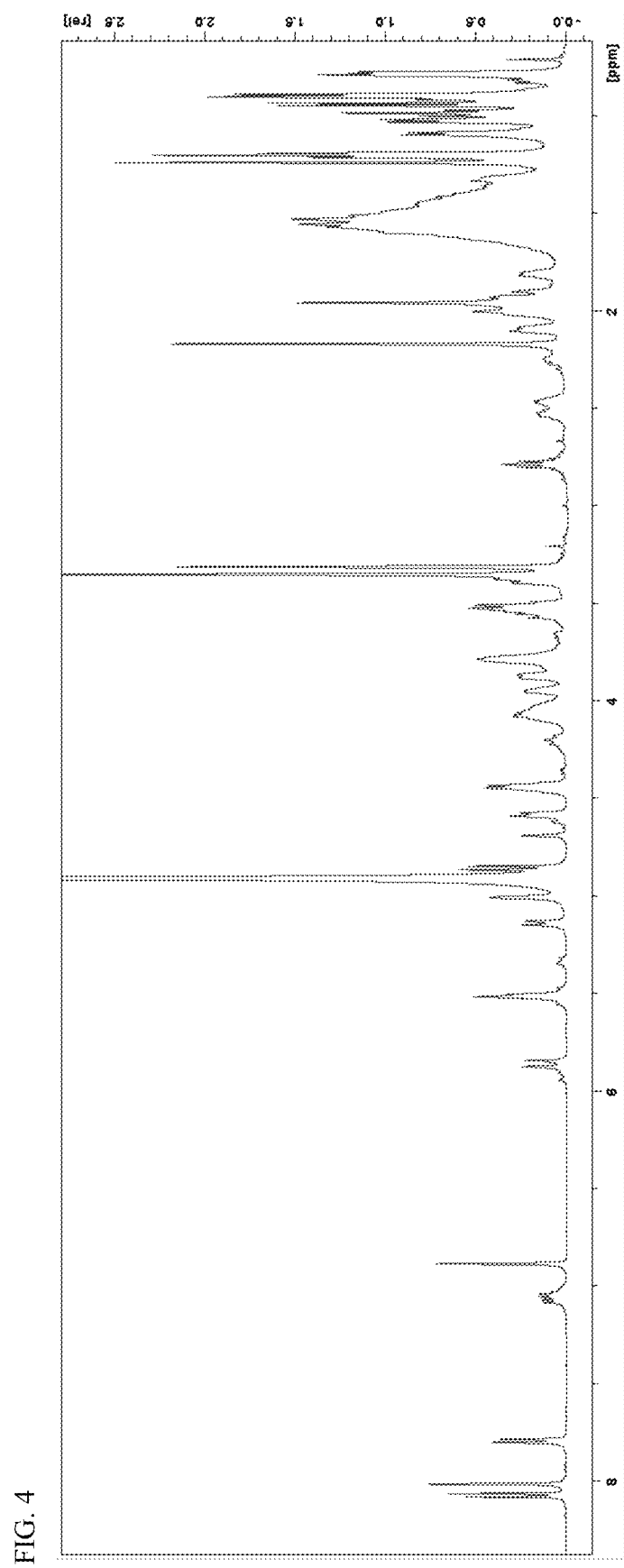
FIG. 4 shows a $^{1}H$ NMR (600 MHz, CDCl$_3$) spectrum of cyphomycin.
Figure 6:
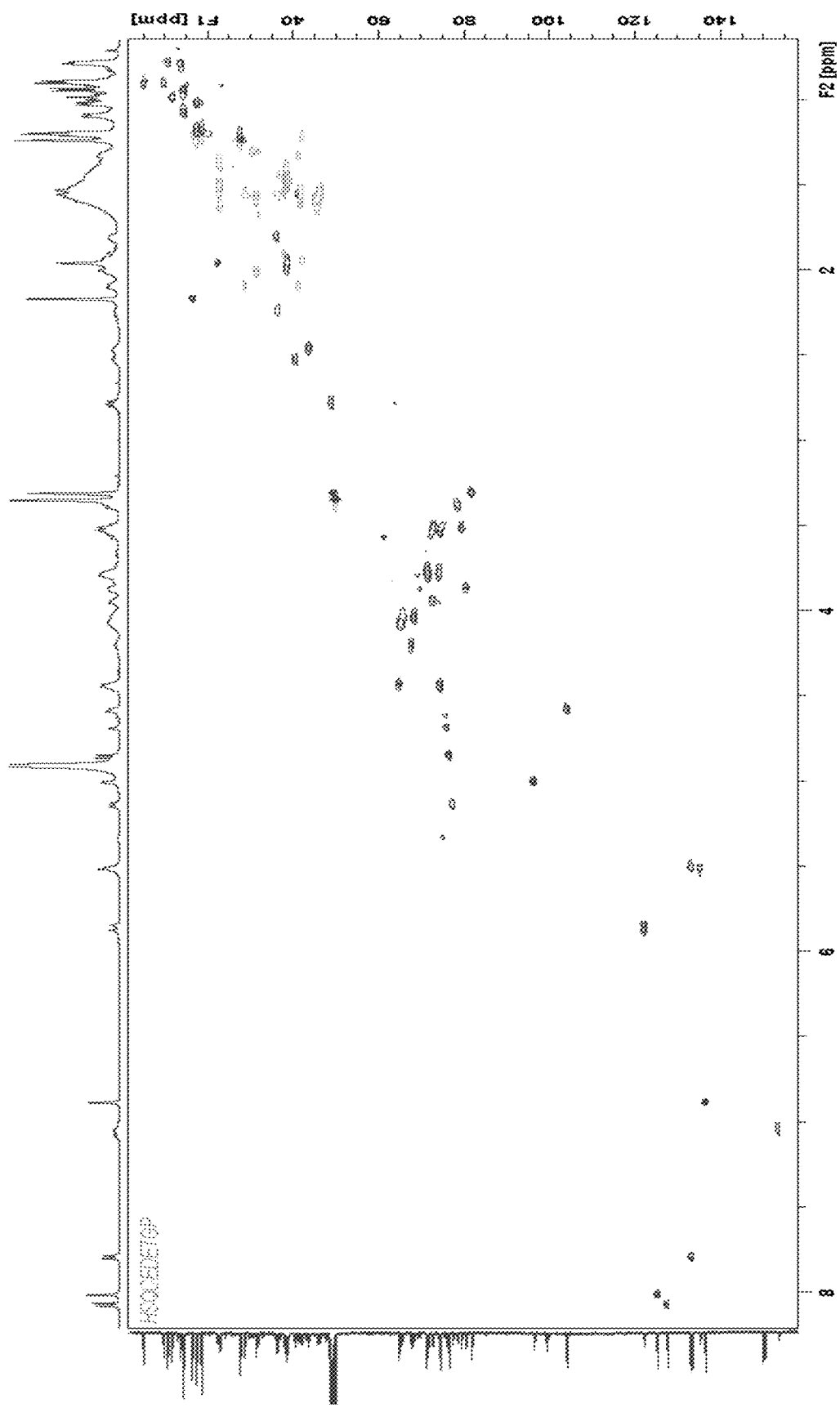
FIG. 6 shows a multiplicity-edited gHSQC (CD$_3$OD, 500 MHz) spectrum of cyphomycin.
Figure 7:
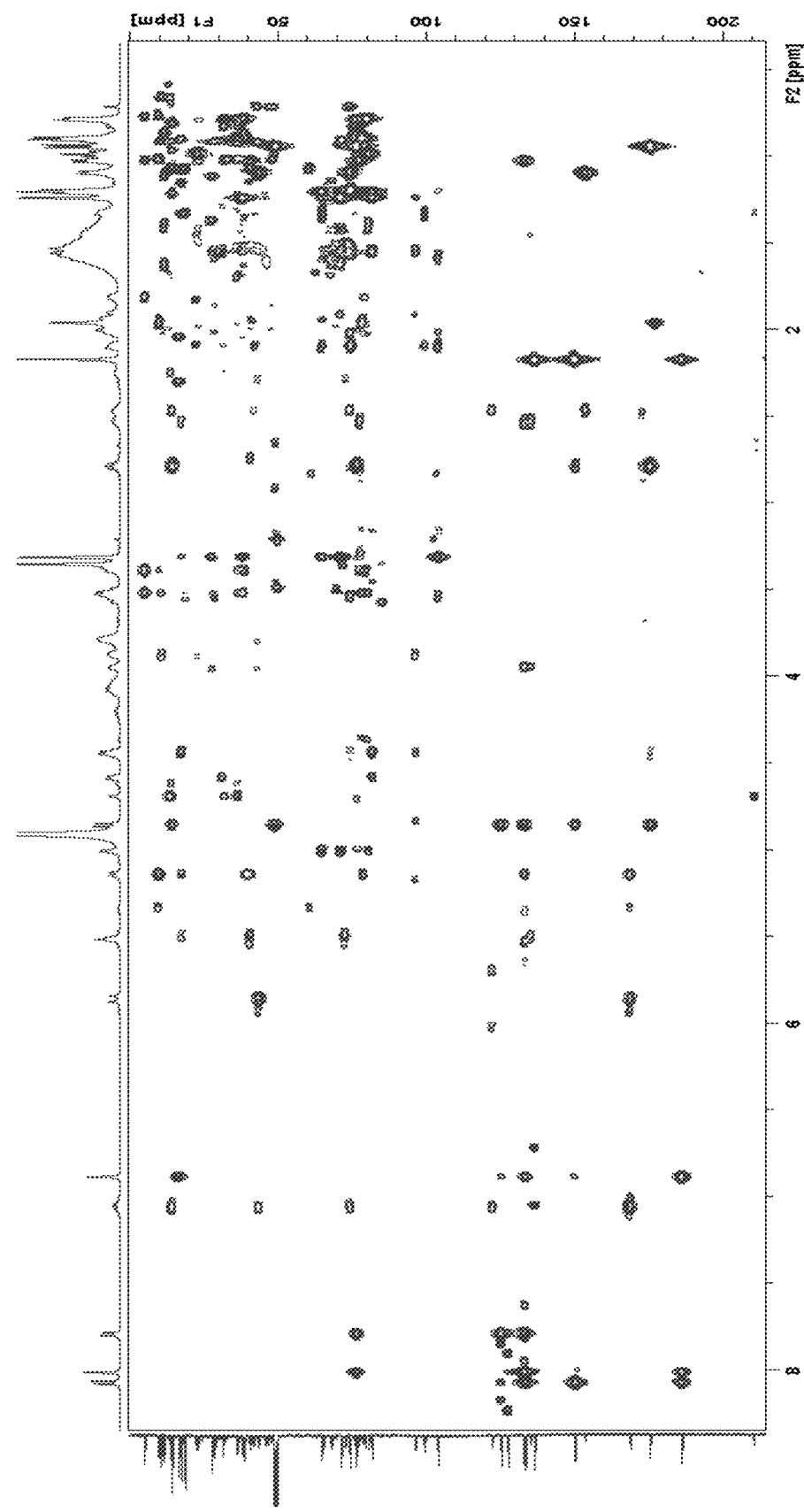
FIG. 7 shows a gHMBC (CD$_3$OD, 500 MHz) spectrum of cyphomycin.
Figure 8:
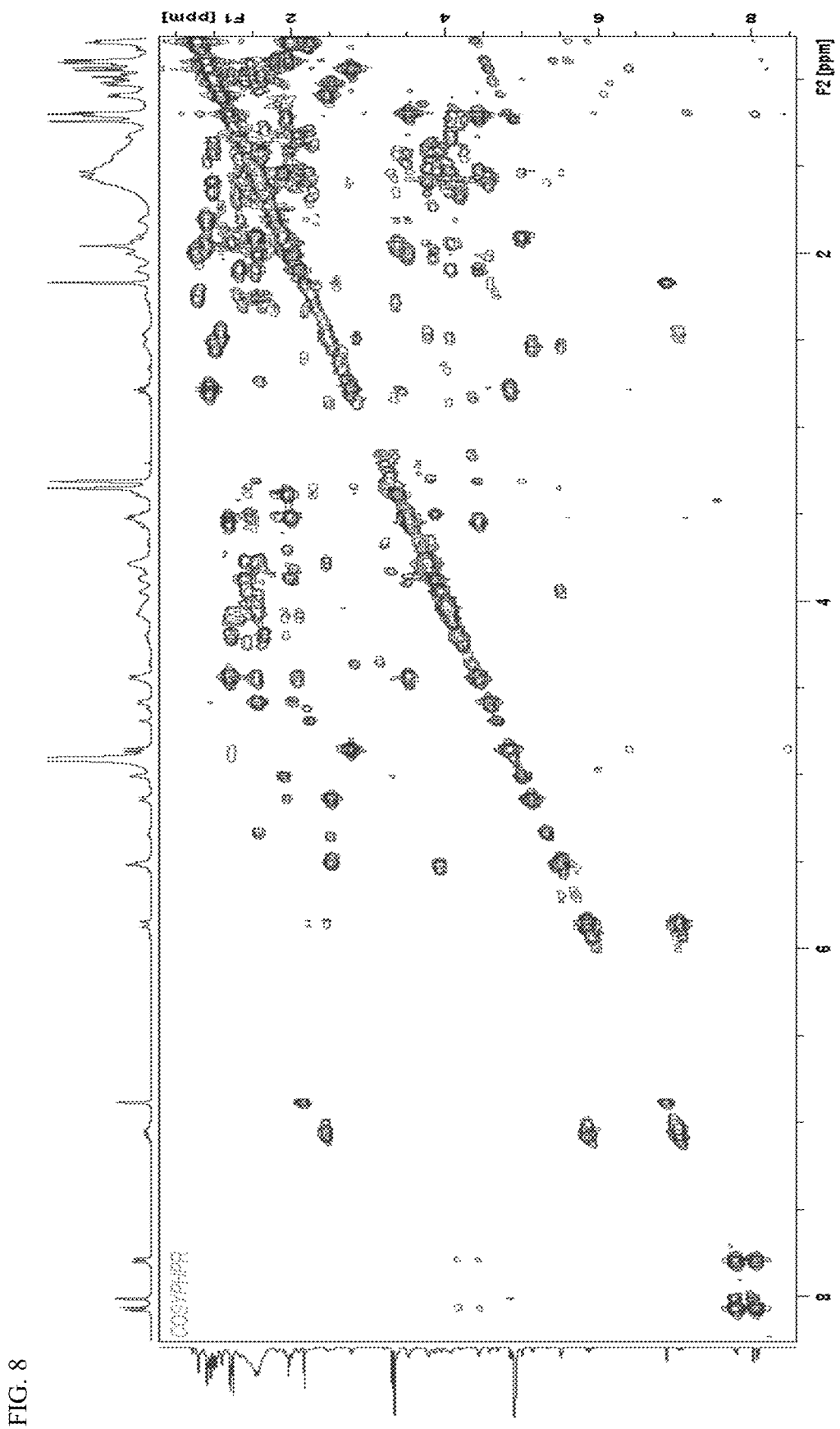
FIG. 8 shows a gCOSY (CD$_3$OD, 500 MHz) spectrum of cyphomycin.
Figure 9:
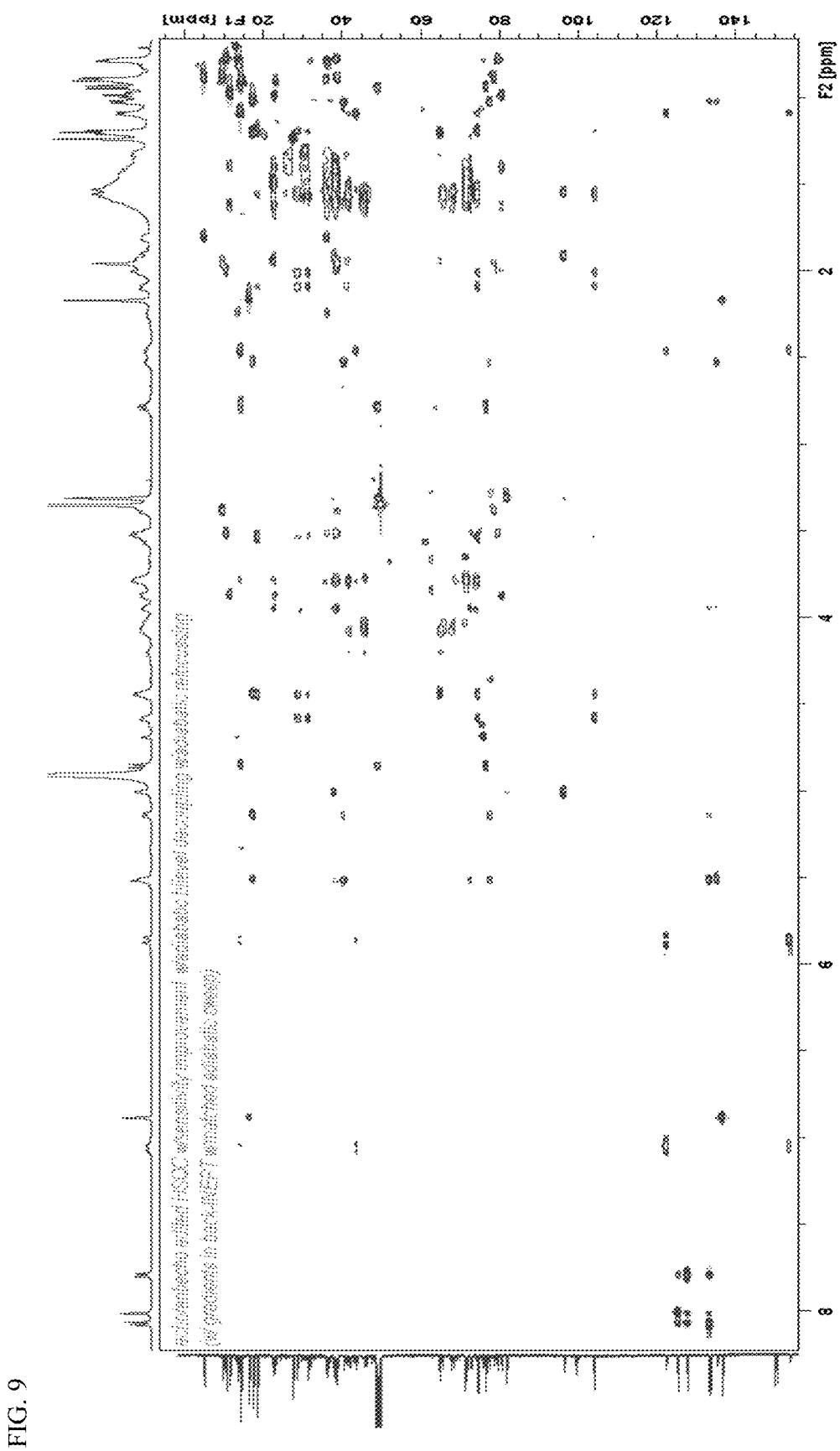
FIG. 9 shows a gHCSQ-TOCSY (CD$_3$OD, 500 MHz) spectrum of cyphomycin.

The $^1$H and $^{13}$C NMR ($CD_3OD$, 500/125 MHz) spectral data of 1 are shown in Table 2 below. The complete $^1$H NMR spectrum of 1 is shown in FIG. 4. The complete $^{13}$C NMR spectrum (FIG. 5) showed 77 signals assigned to 12 methyl, 18 methylene, 36 methine, 5 carbonyl carbons, 4 tertiary carbons sp$^2$ and 2 quaternary carbon groups by multiplicity-edited gHSQC experiment (FIG. 6). COSY and HSQC-TOCSY spectra revealed connectivities from H-2 to H-15 and H-18 to H-43 (FIGS. 8, 9). The connection of these two spin systems was revealed with the HMBC correlation of H-18 ($\delta_H$ 2.09 and 1.33) to C-16 and C-17; H-15 ($\delta_H$ 4.69) to C-16; and H-35 ($\delta_H$ 5.14) to C-1 (FIG. 7). The geometry of the two double bonds of the macrolide moiety were determine to be E configured by the large coupling constants of $^3J_{H\text{-}2,H\text{-}3}$ (15.8 Hz) and $^3J_{H\text{-}32,H\text{-}33}$ (15.6 Hz). The position of methine groups H-4, H-14, H-34, H-36, H-38 and H-40 were assigned by $^1$H-$^1$H COSY correlations to methyl groups H-44, H-45, H-46, H-47, H-48 and H-49, respectively (FIG. 8). The methyl group H-43 was assigned as terminal group of side chain by its triplet multiplicity in $^1$H NMR spectrum and HMBC correlations to C-41 and C-42 (FIGS. 4, 7). The position of oxygenated methine and methylene groups in macrolactone moiety were established by HMBC, COSY and HSQC-TOCSY correlations, and comparison of NMR data of compounds PM100117 and PM100118.[34] The difference in macrolactone moiety of compound 1 versus PM100117/8 is the additional methyl group H-44 attached to C-4. Other 36-member macrolactones are found in axenomycin B,[35a] GT-35[35b] and Depleledes A and B.[35c]

Figure 5:
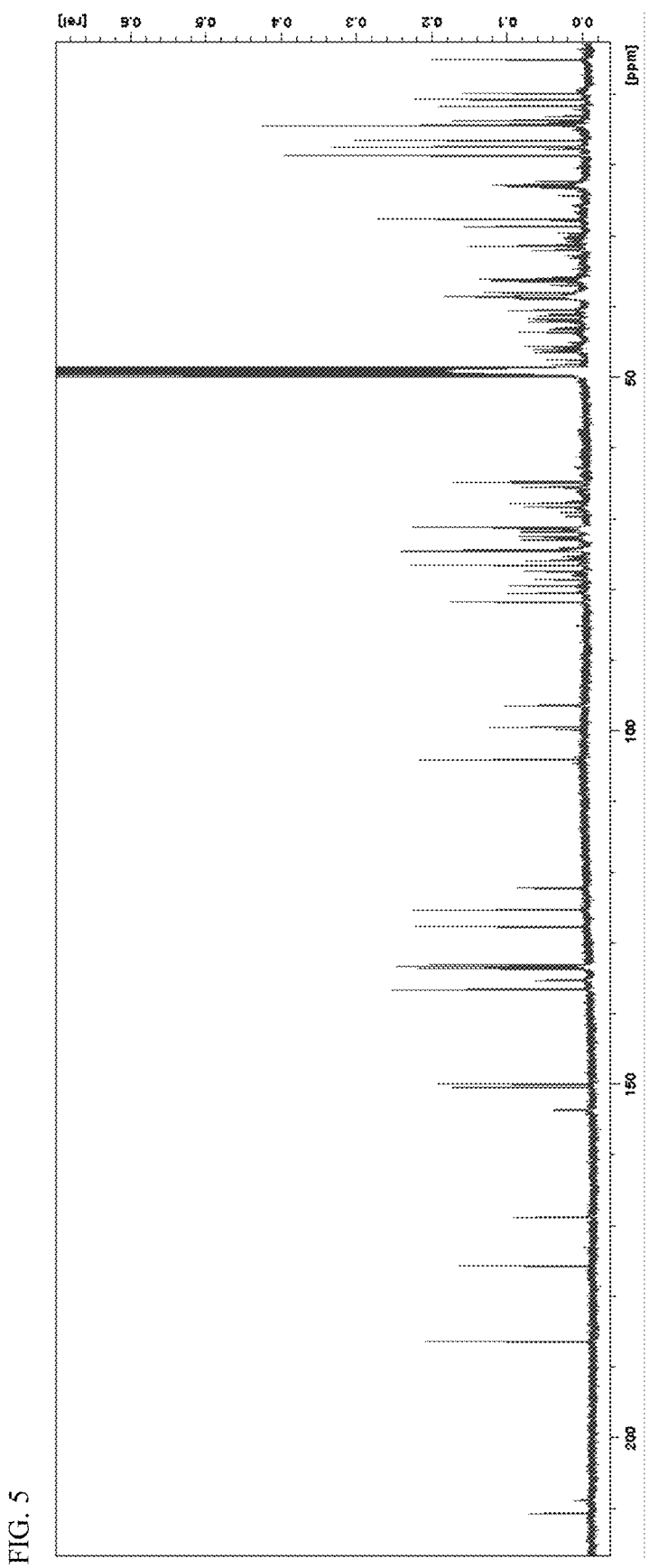
FIG. 5 shows a $^{13}C$ NMR (125 MHz, CDCl$_3$) spectrum of cyphomycin.

The presence of two sugar units was evidenced by $^1$H NMR and $^{13}$C NMR data, mainly signals of two anomeric protons and carbons at $\delta_H$ 5.01 (H-1') and $\delta_H$ 4.58 (H-1"); and $\delta_C$ 96.4 (C-1') and $\delta_C$ 104.0 (C-1"), respectively (FIGS. 4, 5). The first sugar unit was established as $\alpha$-axenose by HMBC, COSY, ROESY correlations (FIG. 14A and FIGS. 7, 8, 10) and NMR data comparison with literature (Perez et al., 2016). There are two $^1$H spin systems from H-1' to H-2' and from H-4' to H-6'; and HMBC correlations from methyl H-7' to C-2', C-3' and C4'. The connection of this sugar to side chain of macrolactone was observed with HMBC correlations of H-1' to C-41 (FIG. 7). The small coupling constant of H-1' and H-4' suggested they should be in equatorial orientation. The ROE correlation of H-41 to H-5' supported the axial orientation of H-5'.

Figure 10:
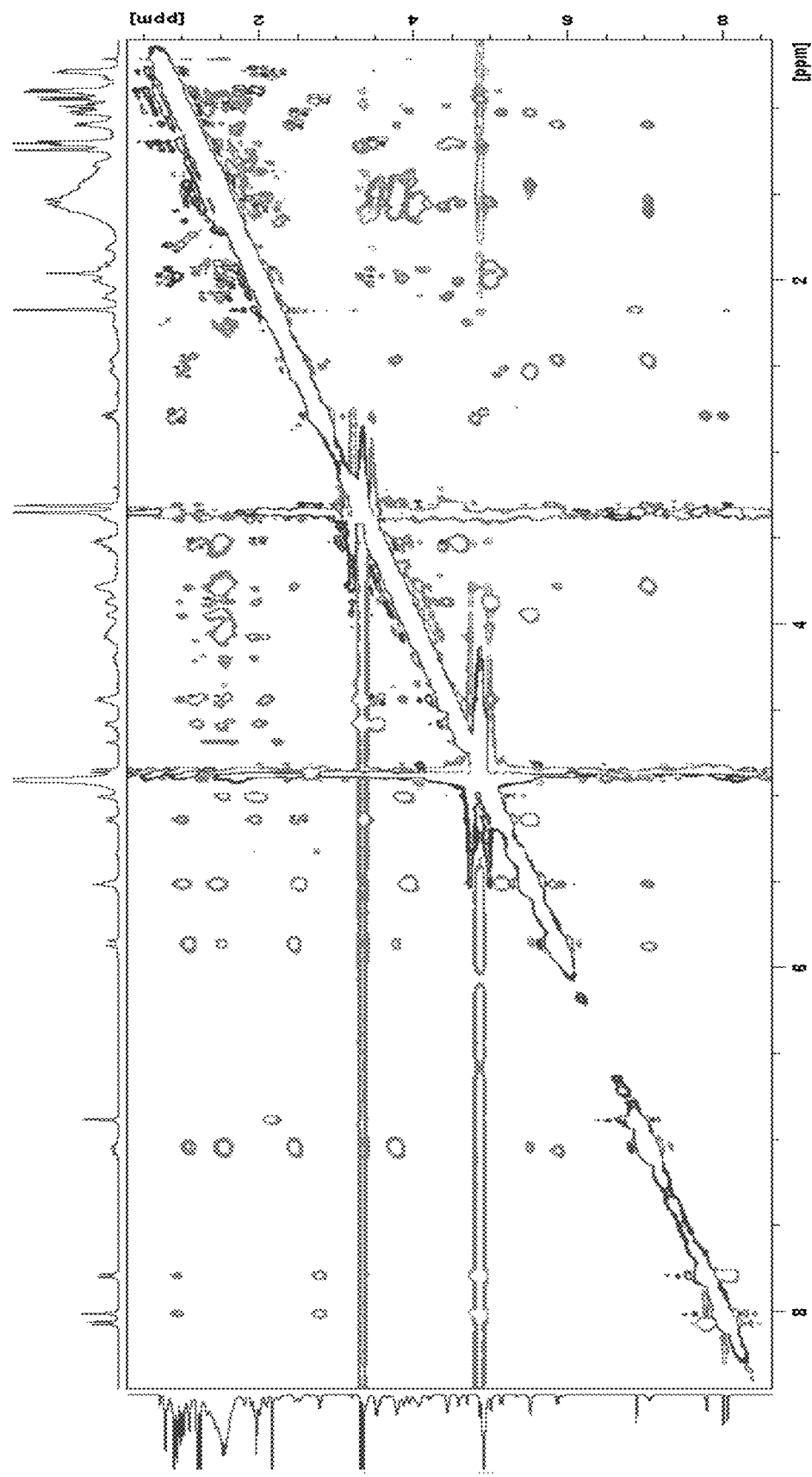
FIG. 10 shows a gROESY (CD$_3$OD, 500 MHz) spectrum of cyphomycin.
Figure 11:
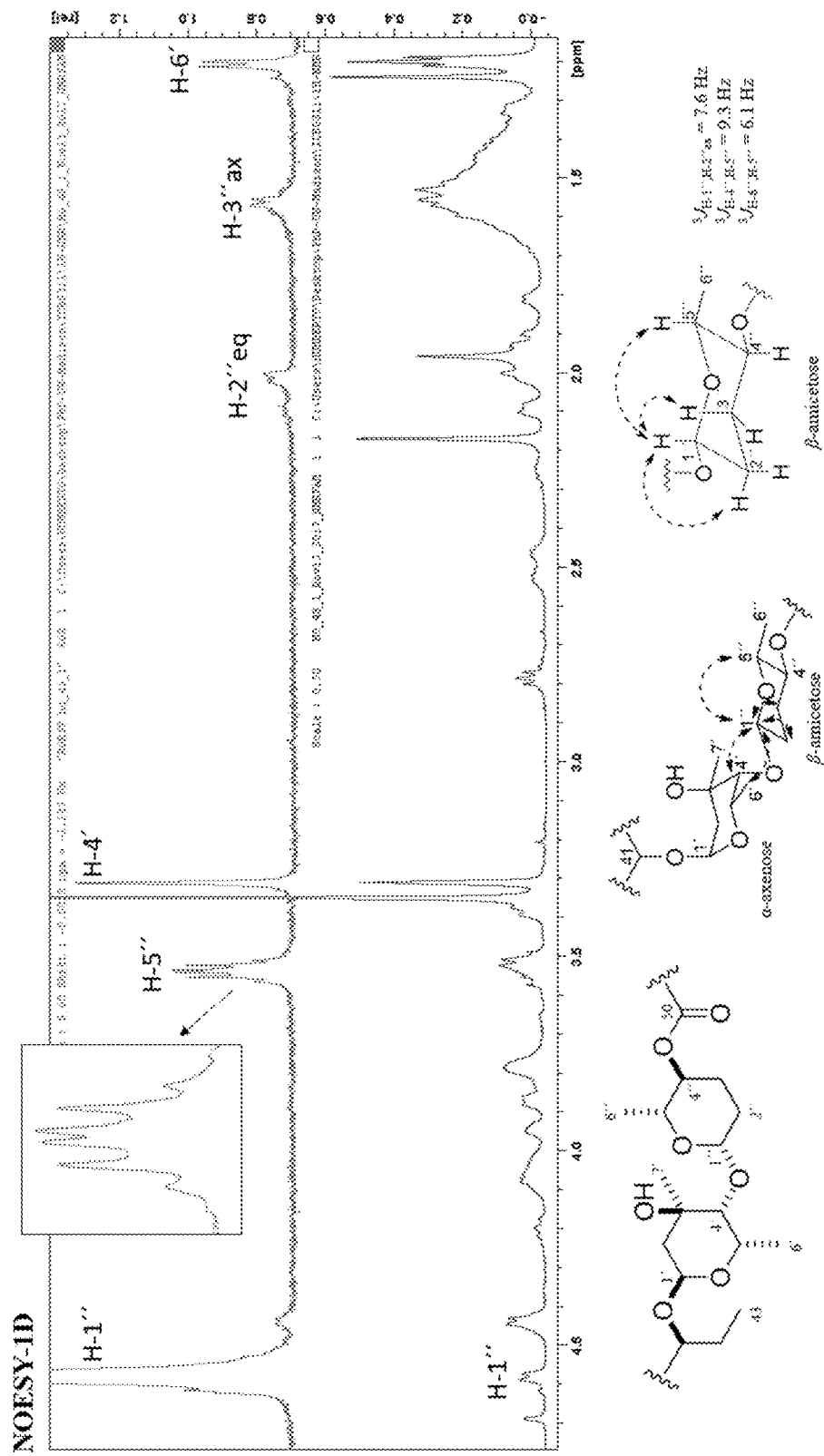
FIG. 11 shows a NOESY-1D (CD$_3$OD, 500 MHz) spectrum of cyphomycin.
Figure 13:
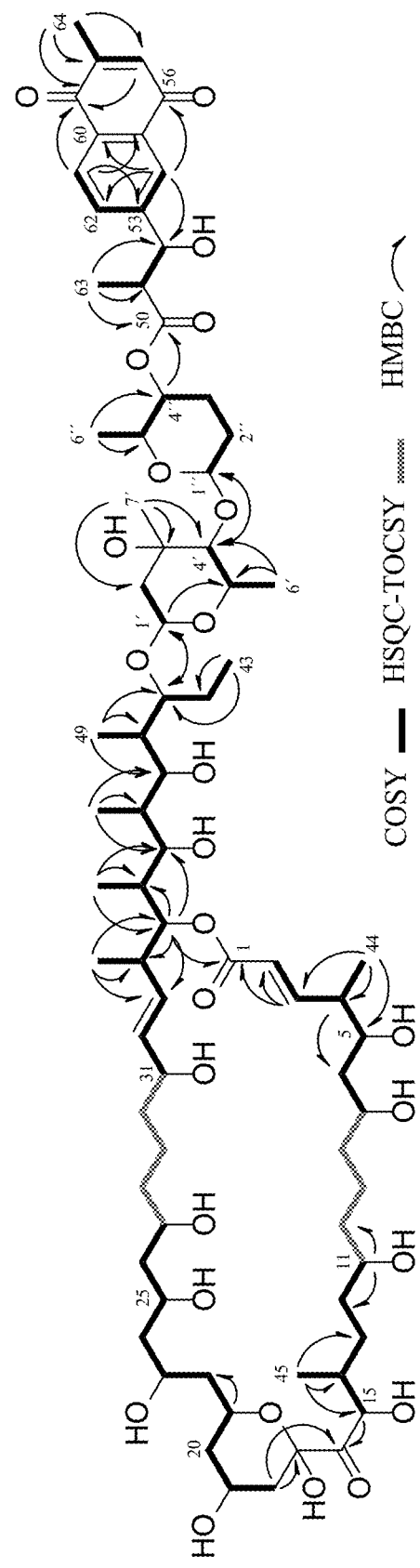
FIG. 13 shows selected COSY, HSQC-TOCSY and HMBC NMR spectral correlations of cyphomycin.
Figure 14:
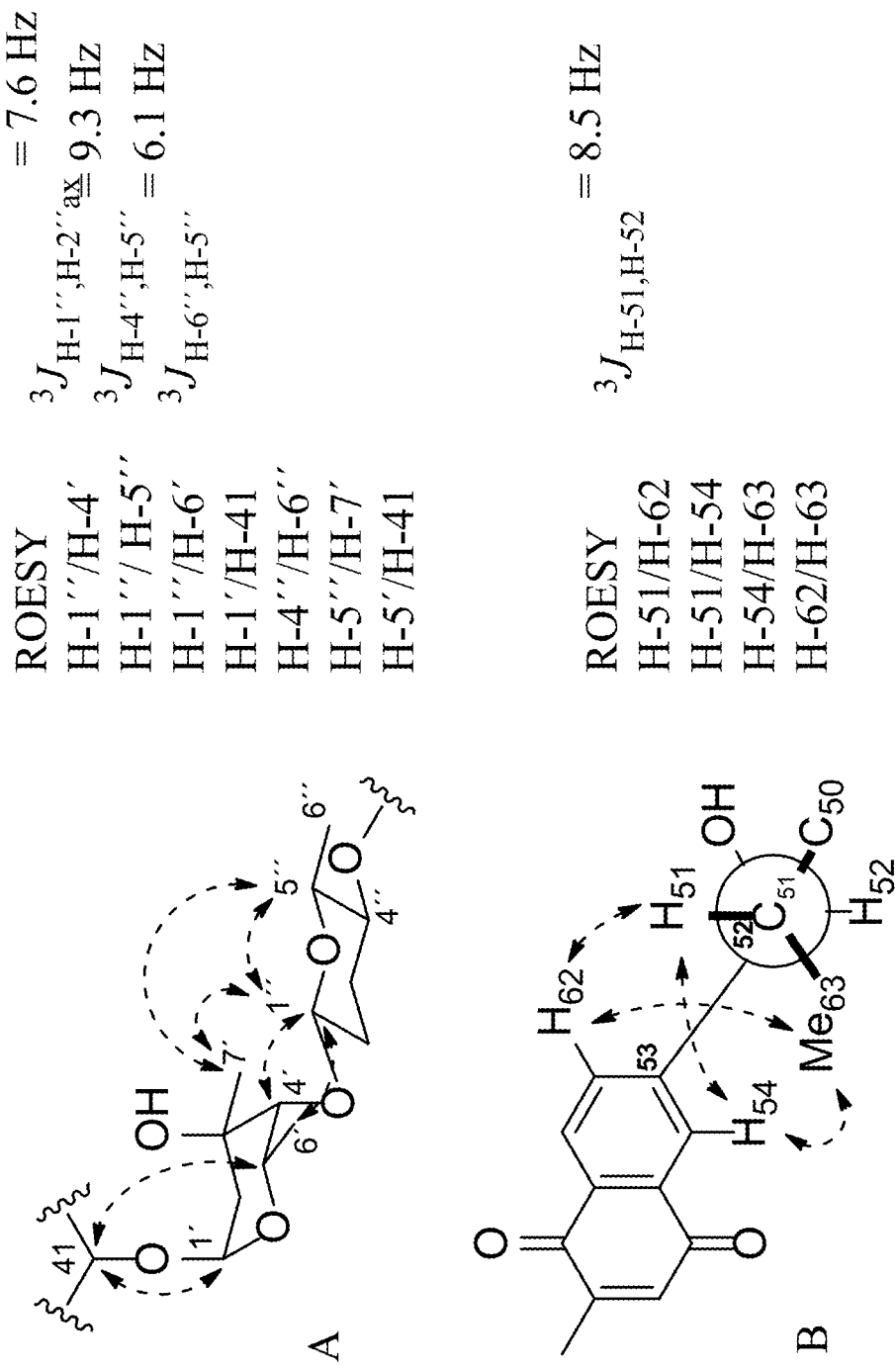
FIGS. 14A-B show relative configuration proposed for fragment: A) disaccharide and B) naphthoquinone units.

The second sugar unit was established as $\beta$-amicetose. The chemical shifts of $\beta$-amicetose were compared to the natural product langkolide (Helaly et al., 2012). This sugar was assigned by the 1H spin system from H-1" to H-6" by HMBC and COSY spectra (FIGS. 7, 8). The large coupling constants $^3J_{H1-",H-2"ax}$ (7.6 Hz) and $^3J_{H-4",H-5"}$ (9.3 Hz); and ROESY/NOESY correlation between H-1" and H-5" (FIGS. 10, 11) suggested the axial orientation of H-1", H-4" and H-5". The connection of both sugars was observed by the HMBC correlation of H-1" to C-4' (FIG. 7). The HMBC correlation of H-4" to C-50 connected the $\beta$-amicetose with naphthoquinone moiety (FIG. 7). $^1$H NMR signals for H-54 ($\delta_H$ 8.01), H-61 ($\delta_H$ 8.07) and H-62 ($\delta_H$ 7.79); $^1$H-$^1$H coupling constants $^3J_{H-54,H-62}$ (1.3 Hz) and $^3J_{H-61,H-62}$ (8.0 Hz); and $^1$H-$^1$H COSY correlations between H-54/H-62 and H-61/H-62 indicated the presence of an aromatic ring trisubstituted moiety (FIG. 4). HMBC correlations of H-54 to C-56; H-61 to C-55 and C-59; H-62 to C-60; H-57 to C-55, C-59 and C-64; and H-64 to C-57, C-58 and C-59 indicated the presence of a quinone moiety methylated in C-58 and connected to the aromatic ring (FIG. 7). HMBC correlation of H-63 to C-50, C-51 and C-52; H-52 to C-50 and C-53; H-54 and H-62 to C-52; evidence the connection of C-50, C-51, C-52, C-53 and C-63 to aromatic ring of naphthoquinone moiety (FIG. 7). The configuration of H-51 as anti with H-52 was determined by a large coupling constant $^3J_{H-51,H-52}$ (8.5 Hz) and $^1$H-$^1$H ROESY correlations between H-51/H-54, H-51/H-62, H-62/H-63 and H-54/H-63 (FIG. 14B and FIGS. 4, 10). The UV spectrum of cyphomycin was similar to that for PM100117 and PM100118 (Pérez et al., 2016) and Depleledes A (Takeuchi et al., 2017), supporting the presence of same naphthoquinone derivative in cyphomycin. The key COSY, HSQC-TOCSY and HMBC correlations of cyphomycin are shown in FIG. 13. An extensive NMR and MS analysis suggested that compound cyphomycin is a new macrolide natural product (Formulae I and IA).

Figure 12:
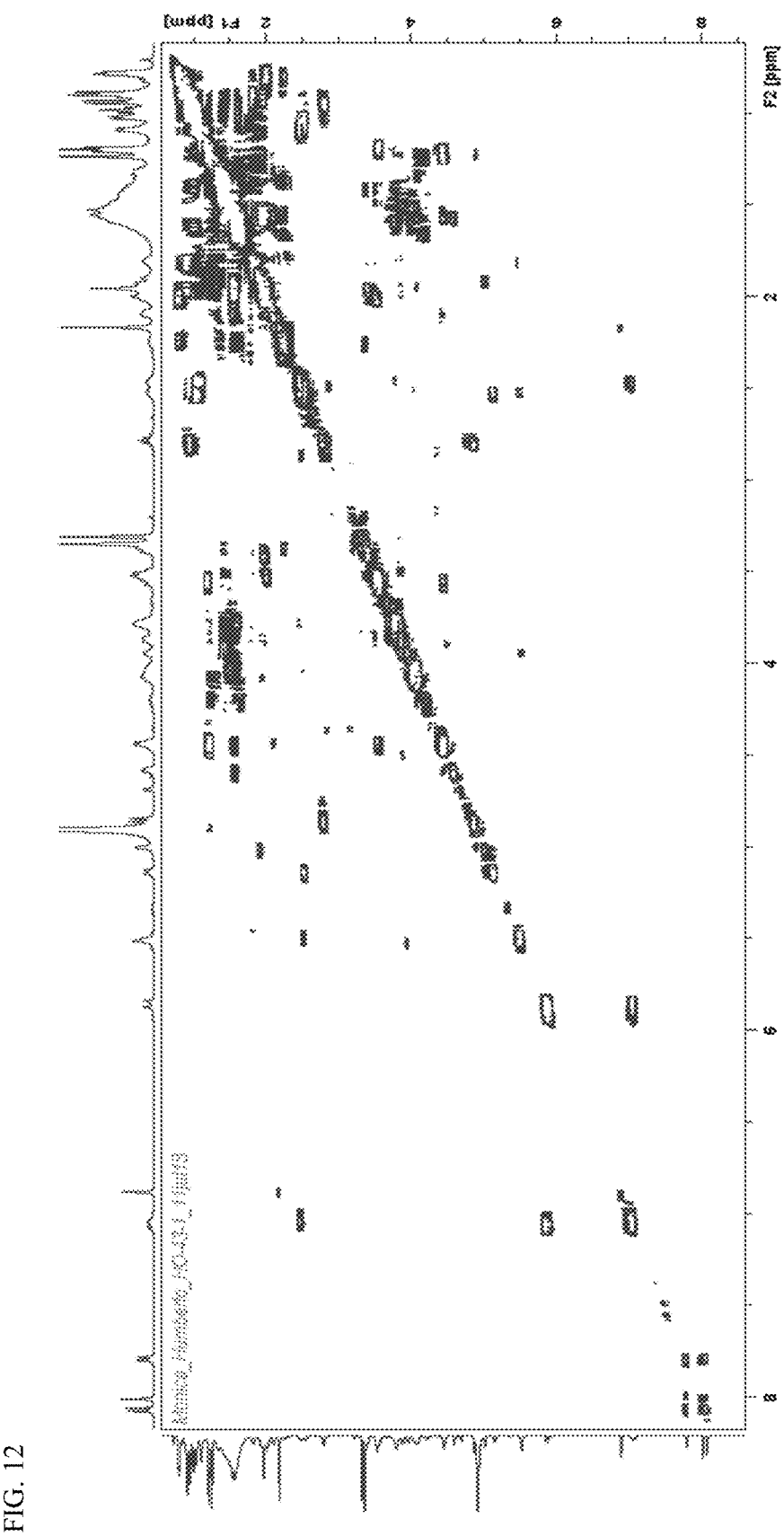
FIG. 12 shows an E. COSY (CD$_3$OD, 600 MHz) of cyphomycin.
Figure 15:
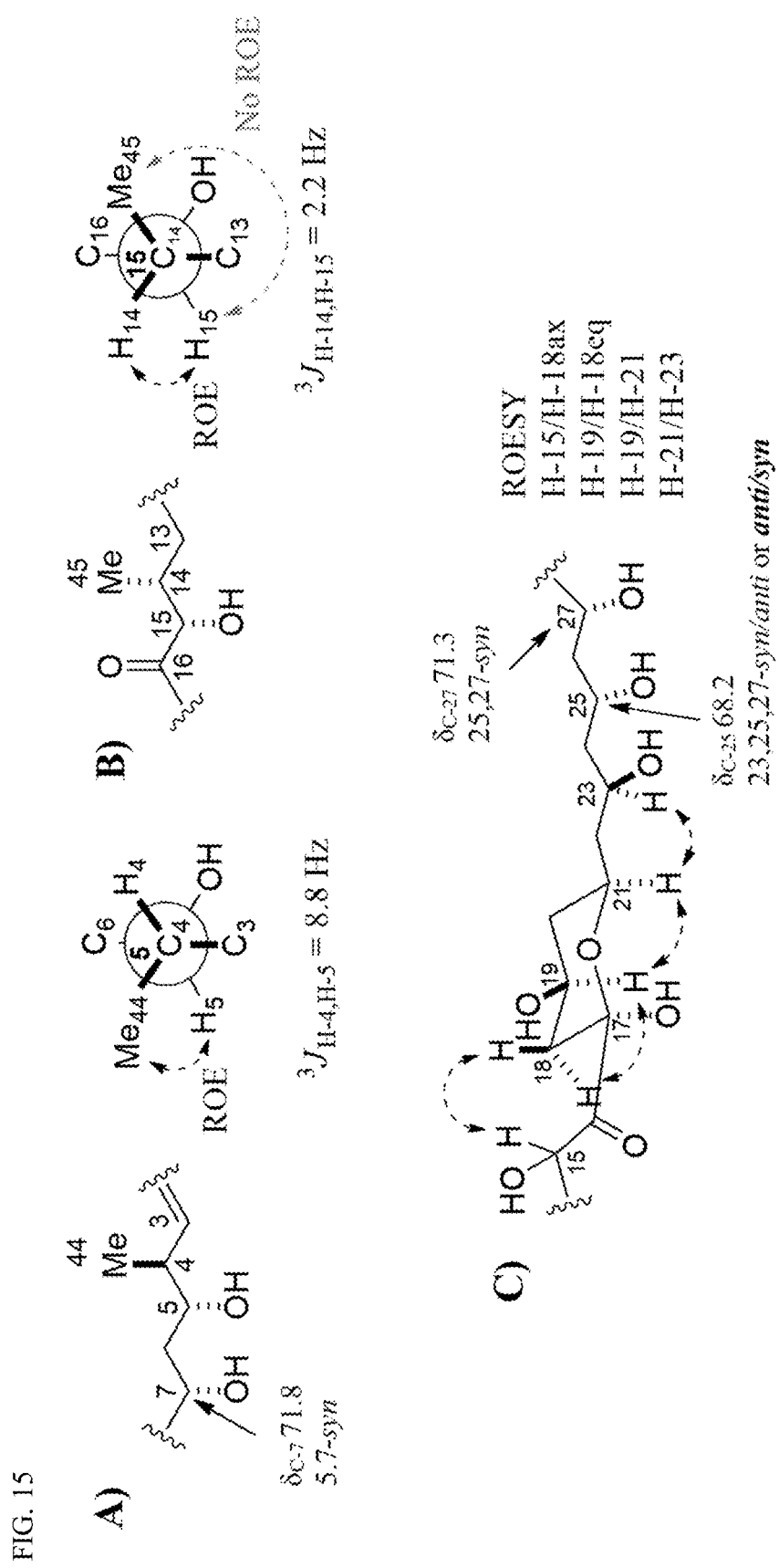
FIGS. 15A-C show relative configuration proposed for fragments: A) C-4 to C-7, B) C-14 to C-15, and C) C-17 to C-27.

The partial relative configuration of macrolactone moiety of cyphomycin was determined using ROESY (FIG. 10), NOESY-1D (FIG. 11), E. COSY (FIG. 12), J-based configuration analysis and Kishi's universal NMR database method (Kobayashi et al. 1999; Kobayashi et al. 2000). The coupling constants were measured by $^1$H NMR and E. COSY spectra (FIGS. 4, 12). The $^1$H-$^1$H ROESY correlation of H-5/H-44 (FIG. 10), large coupling constant $^3J_{H-4,H-5}$ (8.8 Hz) (FIGS. 4, 12) and NMR data comparison with deplelide A (Takeuchi et al., 2017) indicated a 5,44-syn configuration (FIG. 15A). The configuration of C-5 as syn with C-7 was proposed based in shift of C-7 ($\delta_{C-7}$ 71.8) and data set I of Kishi's universal NMR data base. The $^1$H-$^1$H ROESY correlation of H-14/H-15; the no ROE correlation of H-15/H-45; and small coupling constant $^3J_{H-14,H-15}$ (2.2 Hz) suggested the syn configuration of H-14 with H-15 (FIG. 15B). The $^1$H-$^1$H ROESY correlation of H-18ax/H-15, H-18eq/H-19, H-19/H-21 and H-21/H-23 inferred a chair conformation of the tetrahydropyran moiety with equatorial substituents, C-16, 19-OH and C-22, and axial hydroxyl group at C-17 (FIG. 15C). The relative configuration of oxymethine carbons C-23, C-25 and C-27 were assigned as anti/syn using $^{13}$C NMR signals ($\delta_C$ 65.4, 68.2 and 71.3, respectively) and data set I and II of Kishi's universal NMR data base.

The $^1$H-$^1$H ROESY correlation of H-33/H-35, H-35/H-46, H-35/H-36, H-34/H-47, H-37/H-47, H-37/H-38, H-38/H-39, H-38/H-49, H-39/H-49, H-40/H-48, H-40/H41 and H-41/H-1' (FIG. 10 and FIG. 16); the absence of $^1$H-$^1$H ROESY correlation of H-35/H-47, H-39/H-48 and H-41/H-49; the large coupling constants $^3J_{H-34,H-35}$ (9.5 Hz), $^3J_{H-36,H-37}$ (9.5 Hz) and $^3J_{H-39,H-40}$ (7.4 Hz); small coupling constants $^3J_{H-35,H-36}$, $^3J_{H-37,H-38}$ and $^3J_{H-38,H-39}$; data set III of Kishi's universal NMR data base for configuration of C-37 to C-39 [$\delta_{C-48}$ 5.0, 37,38,39-syn/syn]; and NMR data comparison with deplelide A (Takeuchi et al., 2017) suggested that relative configuration of C-34 to C-41 in cyphomycin is identical as observed for deplelide A.

The presence of two sugar units was evidenced by signal of $^1$H and $^{13}$C NMR of two anomeric protons and carbons at $\delta_H$ 5.01 (H-1') and $\delta_H$ 4.58 (H-1"); and $\delta_C$ 96.4 (C-1') and $\delta_C$ 104.0 (C-1"), respectively. The first was established as $\alpha$-axenose by HMBC, COSY, ROE correlations and NMR data comparison with literature.[34]

There are two $^1$H spin systems from H-1' to H-2' and from H-4' to H-6'; and HMBC correlations from methyl H-7' to C-2', C-3' and C4'. Connection of this sugar to side chain of macrolactone was observed with HMBC correlations of H-1' to C-41. Small coupling constant of H-1' and H-4' suggested they should be in equatorial orientation. ROE correlation of H-41 to H-5' supported axial orientation of H-5'.

The second sugar was established as $\beta$-amicetose. It was constructed by the $^1$H spin system from H-1" to H-6". Large coupling constant $^3J_{H-1",H-2"ax}$ (7.6 Hz) and $^3J_{H-4",H-5"}$ (9.3 Hz); and ROE correlation between H-1" and H-5" suggested axial orientation of H-1', H-4" and H-5". Connection of both sugar was observed by the HMBC correlation of H-1" to C-4'. The HMBC correlation of H-4" to C-50 connected the $\beta$-amicetose with the ester carbonyl group of naphthoquinone derivative moiety. $^1$H NMR signals for H-54 ($\delta_H$ 8.01), H-61 ($\delta_H$ 8.07) and H-62 ($\delta_H$ 7.79); $^1$H-$^1$H coupling constants $^3J_{H-54,H-62}$ (1.3 Hz) and $^3J_{H-61,H}$62 (8.0 Hz); and $^1$H-$^1$H COSY correlations between H-54/H-62 and H-61/H-62 indicated the presence of an aromatic ring trisubstituted moiety. HMBC correlations of H-54 to C-56; H-61 to C-55 and C-59; H-62 to C-60; H-57 to C-55, C-59 and C-64; and H-64 to C-57, C-58 and C-59 indicated the presence of a quinone moiety methylated in C-58 and connected to the aromatic ring. HMBC correlation of H-63 to C-50, C-51 and C-52; H-52 to C-50 and C-53; H-54 and H-62 to C-52; evidence the connection of C-50, C-51, C-52, C-53 and C-63 to aromatic ring of naphthoquinone moiety. Compound 1 was named cyphomycin.

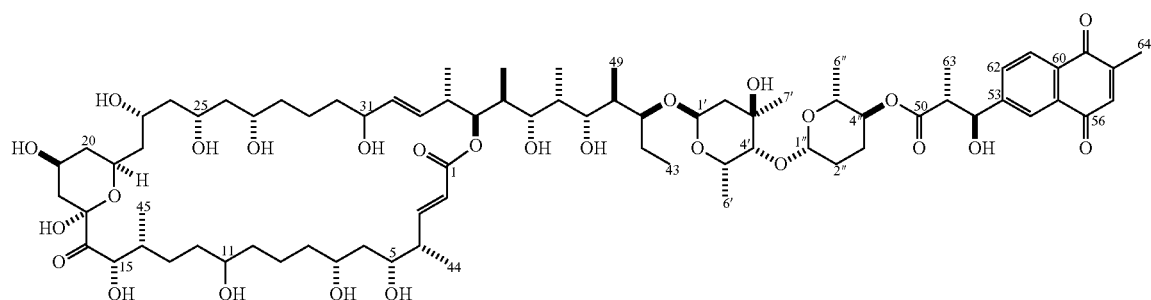

TABLE 2

$^1$H and $^{13}$C NMR (MeOH-$d_4$, 500/125 MHz) cyphomycin data

| No. | $\delta_C$ | $\delta_H$, mult. (J in Hz) |
|---|---|---|
| 1 | 168.7 | — |
| 2 | 122.1 | 5.86, br d (15.8) |
| 3 | 153.5 | 7.06, dd (15.8, 6.8) |
| 4 | 43.5 | 2.47, m |
| 5 | 74.2 | 3.78, m |
| 6 | 41.7 | 1.60, m |
|  |  | 1.54, m |
| 7 | 71.8 | 3.78, m |
| 8 | 38.9 | 1.32-1.62, m |
| 9 | 23.0 | 1.45-1.68, m |
| 10 | 38.5 | 1.32-1.62, m |
| 11 | 72.9 | 3.51, m |
| 12 | 36.4 | 1.38-1.47, m |
|  |  | 1.53-1.63 m |
| 13 | 31.9 | 1.69, m |
|  |  | 1.30, m |
| 14 | 36.2 | 2.25, m |
| 15 | 75.8 | 4.69, d (2.2) |
| 16 | 210.6 | — |
| 17 | 99.4 | — |
| 18 | 41.1 | 2.09, m |
|  |  | 1.33, m |
| 19 | 64.9 | 4.08, m |
| 20 | 42.0 | 1.96, m |
|  |  | 1.21, m |
| 21 | 67.7 | 4.20, m |
| 22 | 45.6 | 1.45-1.74, m |
| 23 | 65.4 | 4.08, m |
| 24 | 46.3 | 1.43-1.67, m |
| 25 | 68.2 | 4.04, m |
| 26 | 46.0 | 1.40-1.76, m |
| 27 | 71.3 | 3.79, m |
| 28 | 38.4 | 1.32-1.62, m |
| 29 | 22.7 | 1.51, m |
| 30 | 38.4 | 1.32-1.62, m |
| 31 | 72.4 | 3.94, m |
| 32 | 135.2 | 5.53, dd (15.6, 4.5) |
| 33 | 133.1 | 5.49, dd (15.6, 7.2) |
| 34 | 40.4 | 2.54, m |
| 35 | 77.3 | 5.14, br d (9.5) |
| 36 | 38.7 | 1.97, m |
| 37 | 78.5 | 3.39, br d (9.5) |
| 38 | 36.0 | 1.81, m |
| 39 | 79.4 | 3.52, m |
| 40 | 38.5 | 2.00, m |
| 41 | 80.5 | 3.88, m |
| 42 | 22.9 | 1.64, m |
|  |  | 1.36, m |
| 43 | 11.5 | 0.98, t (7.2) |
| 44 | 14.1 | 1.09, d (6.7) |
| 45 | 13.6 | 0.79, d (6.4) |
| 46 | 17.3 | 1.03, d (6.5) |
| 47 | 9.7 | 0.90, d (6.8) |
| 48 | 5.0 | 0.90, d (6.8) |
| 49 | 10.6 | 0.78, d (6.4) |
| 1' | 96.4 | 5.01, br s |
| 2' | 37.9 | 1.93, dd (3.70, 14.0) |
|  |  | 1.55, d (14.0) |
| 3' | 71.2 | — |
| 4' | 81.7 | 3.31, m |
| 5' | 64.7 | 4.44, m |
| 6' | 17.3 | 1.21, d (6.6) |
| 7' | 27.5 | 1.24, s |
| 1" | 104.0 | 4.58, br d (7.6) |
| 2" | 31.3 | 2.01, m |
|  |  | 1.56, m |
| 3" | 28.6 | 2.10, m |
|  |  | 1.56, m |
| 4" | 74.4 | 4.45, m |
| 5" | 74.5 | 3.54, dq (6.1, 9.3) |
| 6" | 18.5 | 1.19, d (6.1) |
| 50 | 175.5 | — |
| 51 | 48.9 | 2.78, dq (8.5, 7.1) |
| 52 | 76.4 | 4.86, d (8.5) |
| 53 | 150.3 | — |
| 54 | 125.3 | 8.01, br s |
| 55 | 133.5 | — |
| 56 | 186.2 | — |
| 57 | 136.5 | 6.88, br d (1.4) |
| 58 | 149.8 | — |
| 59 | 186.3 | — |
| 60 | 132.9 | — |
| 61 | 127.6 | 8.07, d (8.0) |
| 62 | 133.2 | 7.79, dd (8.0, 1.3) |
| 63 | 14.3 | 0.94, d (7.1) |
| 64 | 16.4 | 2.17, s |

REFERENCES

1. Sprenger, M. & Fukuda, K. New mechanisms, new worries. *Science* 351, 1263-1264 (2016).
2. Brown, E. D. & Wright, G. D. Antibacterial drug discovery in the resistance era. *Nature* 529, 336-343 (2016).
3. Newman, D. J. & Cragg, G. M. Natural products as sources of new drugs from 1981 to 2014. *J. Nat. Prod.* 79, 629-661 (2016).
4. Baltz, R. H. Marcel Faber Roundtable: Is our antibiotic pipeline unproductive because of starvation, constipation or lack of inspiration? *J. Ind. Microbiol. Biotechnol.* 33, 507-513 (2006).
5. Medema, M. H., Cimermancic, P., Sali, A., Takano, E. & Fischbach, M. A. A systematic computational analysis of biosynthetic gene cluster evolution: lessons for engineering biosynthesis. *PLoS Comput. Biol.* 10, e1004016 (2014).
6. Doroghazi, J. R. et al. A roadmap for natural product discovery based on large-scale genomics and metabolomics. *Nat. Chem. Biol.* 10, 963-968 (2014).

7. Smanski, M. J. et al. Synthetic biology to access and expand nature's chemical diversity. *Nat. Rev. Microbiol.* 14, 135-149 (2016).
8. Udwary, D. W. et al. Genome sequencing reveals complex secondary metabolome in the marine actinomycete *Salinispora tropica*. *Proc. Natl. Acad. Sci.* 104, 10376-10381 (2007).
9. Ziemert, N. et al. Diversity and evolution of secondary metabolism in the marine actinomycete genus *Salinispora*. *Proc. Natl. Acad. Sci.* 111, E1130-9 (2014).
10. Jang, K. H. et al. Anthracimycin, a Potent Anthrax Antibiotic from a Marine-Derived Actinomycete. *Angew. Chemie Int. Ed.* 52, 7822-7824 (2013).
11. Schulze, C. J. et al. Genome-Directed Lead Discovery: Biosynthesis, Structure Elucidation, and Biological Evaluation of Two Families of Polyene Macrolactams against *Trypanosoma brucei*. *ACS Chem. Biol.* 150813113920008 (2015). doi:10.1021/acschembio.5b00308
12. Ling, L. L. et al. A new antibiotic kills pathogens without detectable resistance. *Nature* 517, 455-459 (2015).
13. Pye, C. R., Bertin, M. J., Lokey, R. S., Gerwick, W. H. & Linington, R. G. Retrospective analysis of natural products provides insights for future discovery trends. *Proc. Natl. Acad. Sci.* 114, 5601-5606 (2017).
14. Miller, I., Chevrette, M. & Kwan, J. Interpreting microbial biosynthesis in the genomic age: biological and practical considerations. *Mar. Drugs* 15, 165 (2017).
15. Clardy, J., Fischbach, M. a. & Currie, C. R. The natural history of antibiotics. *Curr. Biol.* 19, 1-8 (2009).
16. Adnani, N. et al. Coculture of Marine Invertebrate-Associated Bacteria and Interdisciplinary Technologies Enable Biosynthesis and Discovery of a New Antibiotic, Keyicin. *ACS Chem. Biol.* 12, 3093-3102 (2017).
17. Zipperer, A. et al. Human commensals producing a novel antibiotic impair pathogen colonization. *Nature* 535, 511-6 (2016).
18. Oh, D.-C., Poulsen, M., Currie, C. R. & Clardy, J. Dentigerumycin: a bacterial mediator of an ant-fungus symbiosis. *Nat. Chem. Biol.* 5, 391-393 (2009).
19. Currie, C. R. et al. Ancient tripartite coevolution in the attine ant-microbe symbiosis. *Science* 299, 386-388 (2003).
20. VanArnam, E. B. et al. Selvamicin, an atypical antifungal polyene from two alternative genomic contexts. *Proc. Natl. Acad. Sci.* 113, 12940-12945 (2016).
21. Kroiss, J. et al. Symbiotic streptomycetes provide antibiotic combination prophylaxis for wasp offspring. *Nat. Chem. Biol.* 6, 261-263 (2010).
22. Scott, J. J. et al. Bacterial Protection of Beetle-Fungus Mutualism. *Science* 322, 63-63 (2008).
23. Stork, N. E., McBroom, J., Gely, C. & Hamilton, A. J. New approaches narrow global species estimates for beetles, insects, and terrestrial arthropods. *Proc. Natl. Acad. Sci.* 112, 7519-23 (2015).
24. Eisner, T. & Meinwald, J. Defensive secretions of arthropods. *Science* 153, 1341-50 (1966).
25. Book, A. J. et al. Evolution of high cellulolytic activity in symbiotic *Streptomyces* through selection of expanded gene content and coordinated gene expression. *PLoS Biol.* 14, 1-21 (2016).
26. Blodgett, J. A. V. et al. Common biosynthetic origins for polycyclic tetramate macrolactams from phylogenetically diverse bacteria. *Proc. Natl. Acad. Sci.* 107, 11692-11697 (2010).
27. Oh, D. C., Poulsen, M., Currie, C. R. & Clardy, J. Sceliphrolactam, a polyene macrocyclic lactam from a wasp-associated *Streptomyces* sp. *Org. Lett.* 13, 752-755 (2011).
28. Carr, G. et al. Microtermolides A and B from termite-associated *Streptomyces* sp. and structural revision of vinylamycin. *Org. Lett.* 14, 2822-5 (2012).
29. Chevrette, M. G. & Currie, C. R. Emerging evolutionary paradigms in antibiotic discovery. *J. Ind. Microbiol. Biotechnol.* (2018). doi:10.1007/s10295-018-2085-6
30. Hug, J., Bader, C., Remškar, M., Cirnski, K. & Müller, R. Concepts and Methods to Access Novel Antibiotics from Actinomycetes. *Antibiotics* 7, 44 (2018).
31. McDonald, B. R. & Currie, C. R. Lateral gene transfer dynamics in the ancient bacterial genus *Streptomyces*. *MBio* 8, e00644-17 (2017).
32. Blin, K. et al. antiSMASH 4.0—improvements in chemistry prediction and gene cluster boundary identification. *Nucleic Acids Res.* 1854, 1019-1037 (2017).
33. https://git.wageningenur.nl/medema-group/BiGSCAPE/.
34. Pérez, M. et al. PM100117 and PM100118, new antitumor macrolides produced by a marine *Streptomyces caniferus* GUA-06-05-006A. *J. Antibiot.* 69, 388-394 (2016).
35. a) Arcamone, F. et al. Axenomycins. I. The Structure of Chromophore and Sugar moieties. *Journal of the American Chemical Society.* https://doi.org/10.1021/ja00787a048 (1973); b) Takahashi et al. Fungicidal GT35 manufacture with *Streptomyces*. Retrieved from http://www.sumobrain.com/patents/jp/New-substance-gt35-its-production/JPH09100290A.html (1997); c) Takeuchi, T. et al. ATP depletion assay led to the isolation of new 36-membered polyol macrolides Deplelides A and B from *Streptomyces* sp. MM581-NF15. *Org. Lett.* 19, 4207-4210 (2017).
36. Zhao, M. et al. In Vivo Pharmacokinetics and Pharmacodynamics of APX001 against *Candida* spp. in a Neutropenic Disseminated Candidiasis Mouse Model. *Antimicrob. Agents Chemother.* 62, e02542-17 (2018).
37. Zhao, M., Lepak, A. J. & Andes, D. R. Animal models in the pharmacokinetic/pharmacodynamic evaluation of antimicrobial agents. *Bioorg. Med. Chem.* 24, 6390-6400 (2016).
38. Andes, D. R. & Lepak, A. J. In vivo infection models in the pre-clinical pharmacokinetic/pharmacodynamic evaluation of antimicrobial agents. *Curr. Opin. Pharmacol.* 36, 94-99 (2017).
39. Payne, D. J. Microbiology. Desperately seeking new antibiotics. *Science* 321, 1644-5 (2008).
40. Fisher, M. C., Hawkins, N. J., Sanglard, D. & Gurr, S. J. Worldwide emergence of resistance to antifungal drugs challenges human health and food security. *Science* 360, 739-742 (2018).
41. Fischbach, M. A. & Walsh, C. T. Antibiotics for emerging pathogens. *Science* 325, 1089-1093 (2009).
42. Hayakawa, M. & Nonomura, H. Humic acid-vitamin agar, a new medium for the selective isolation of soil actinomycetes. *J. Ferment. Technol.* 65, 501-509 (1987).
43. Hanshew, A. S. et al. Characterization of Actinobacteria Associated with Three Ant-Plant Mutualisms. *Microb. Ecol.* 69, 192-203 (2015).
44. Li, Q., Chen, X., Jiang, Y. & Jiang, C. Morphological Identification of Actinobacteria. in *Actinobacteria—Basics and Biotechnological Applications* (InTech, 2016). doi:10.5772/61461

45. Katoh, K. & Standley, D. M. MAFFT Multiple Sequence Alignment Software Version 7: Improvements in Performance and Usability. *Mol. Biol. Evol.* 30, 772-780 (2013).
46. Price, M. N., Dehal, P. S. & Arkin, A. P. FastTree 2—Approximately Maximum-Likelihood Trees for Large Alignments. *PLoS One* 5, e9490 (2010).
47. Benjamini, Y. & Yekutieli, D. The control of the false discovery rate in multiple testing under dependency. *Ann. Stat.* 29, 1165-1188 (2001).
48. Kumar, L. & Futschik, M. E. Mfuzz: A software package for soft clustering of microarray data. *Bioinformation* 2, 5-7 (2007).
49. Liu, Y., Schröder, J. & Schmidt, B. Musket: a multistage k-mer spectrum-based error corrector for Illumina sequence data. *Bioinformatics* 29, 308-15 (2013).
50. Magoč, T. & Salzberg, S. L. FLASH: fast length adjustment of short reads to improve genome assemblies. *Bioinformatics* 27, 2957-63 (2011).
51. Bankevich, A. et al. SPAdes: A New Genome Assembly Algorithm and Its Applications to Single-Cell Sequencing. *J. Comput. Biol.* 19, 455-477 (2012).
52. Hyatt, D. et al. Prodigal: prokaryotic gene recognition and translation initiation site identification. *BMC Bioinformatics* 11, 119 (2010).
53. Eddy, S. R. Accelerated Profile HMM Searches. *PLoS Comput. Biol.* 7, e1002195 (2011).
54. Stamatakis, A. RAxML version 8: A tool for phylogenetic analysis and post-analysis of large phylogenies. *Bioinformatics* 30, 1312-1313 (2014).
55. Medema, M. H. et al. Minimum Information about a Biosynthetic Gene cluster. *Nat. Chem. Biol.* 11, 625-631 (2015).

Equivalents

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of treating a fungal infection comprising administering to a mammal in need thereof an effective amount of a compound, or a pharmaceutical composition thereof, wherein:

the compound is a compound of Formula I,

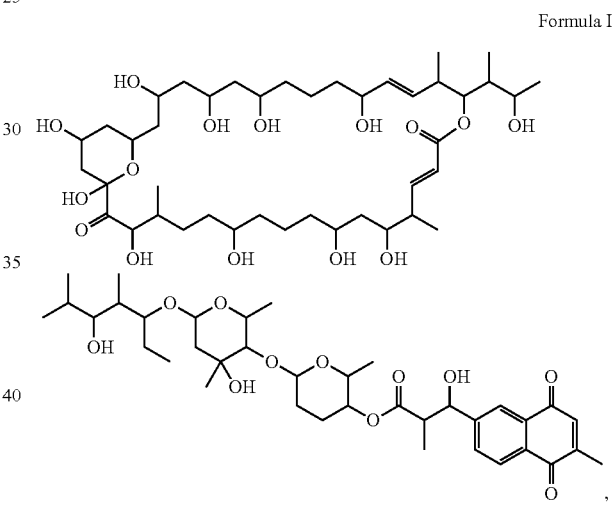

Formula I or the compound is a compound of Formula IA,

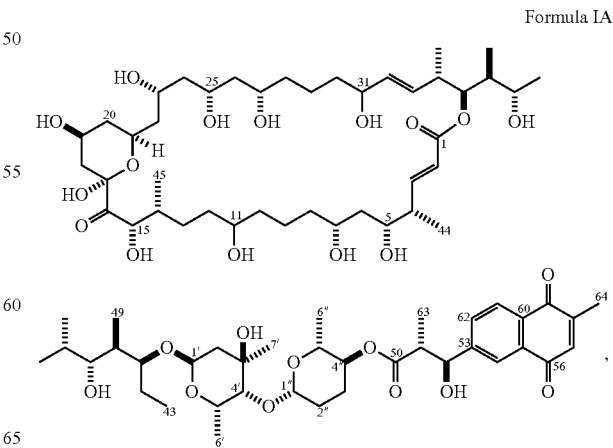

Formula IA or the compound has the formula, $C_{77}H_{122}O_{26}$ and exhibits one or more of the following spectral features:
one or more $^{13}C$ NMR peaks at or about the ppm chemical shifts in the table below;
one or more $^1H$ NMR peaks at or about the ppm chemical shifts in the table below; or
one or more UV $\lambda_{max}$ at about 204, about 248, about 254, or about 334 nm;

| $\delta_C$ | $\delta_H$, mult. (J in Hz) | $\delta_C$ | $\delta_H$, mult. (J in Hz) |
|---|---|---|---|
| 168.7 | — | 38.5 | 2.00, m |
| 122.1 | 5.86, br d (15.8) | 80.5 | 3.88,m |
| 153.5 | 7.06, dd (15.8, 6.8) | 22.9 | 1.64, m |
|  |  |  | 1.36, m |
| 43.5 | 2.47, m | 11.5 | 0.98, t (7.2) |
| 74.2 | 3.78,m | 14.1 | 1.09, d (6.7) |
| 41.7 | 1.60, m | 13.6 | 0.79, d (6.4) |
|  | 1.54, m |  |  |
| 71.8 | 3.78, m | 17.3 | 1.03, d (6.5) |
| 38.9 | 1.32-1.62, m | 9.7 | 0.90, d (6.8) |
| 23.0 | 1.45-1.68, m | 5.0 | 0.90, d (6.8) |
| 38.5 | 1.32-1.62, m | 10.6 | 0.78, d (6.4) |
| 72.9 | 3.51, m | 96.4 | 5.01, br s |
| 36.4 | 1.38-1.47, m | 37.9 | 1.93, dd (3.70, 14.0) |
|  | 1.53-1.63 m |  | 1.55, d (14.0) |
| 31.9 | 1.69,m | 71.2 | — |
|  | 1.30, m |  |  |
| 36.2 | 2.25, m | 81.7 | 3.31, m |
| 75.8 | 4.69, d (2.2) | 64.7 | 4.44, m |
| 210.6 | — | 17.3 | 1.21, d (6.6) |
| 99.4 | — | 27.5 | 1.24, s |
| 41.1 | 2.09,m | 104.0 | 4.58, br d (7.6) |
|  | 1.33, m |  |  |
| 64.9 | 4.08, m | 31.3 | 2.01, m |
|  |  |  | 1.56, m |
| 42.0 | 1.96, m | 28.6 | 2.10, m |
|  | 1.21,m |  | 1.56,m |
| 67.7 | 4.20, m | 74.4 | 4.45, m |
| 45.6 | 1.45-1.74, m | 74.5 | 3.54, dq (6.1, 9.3) |
| 65.4 | 4.08, m | 18.5 | 1.19, d (6.1) |
| 46.3 | 1.43-1.67, m | 175.5 | — |
| 68.2 | 4.04, m | 48.9 | 2.78, dq (8.5, 7.1) |
| 46.0 | 1.40-1.76, m | 76.4 | 4.86, d (8.5) |
| 71.3 | 3.79, m | 150.3 | — |
| 38.4 | 1.32-1.62, m | 125.3 | 8.01, br s |
| 22.7 | 1.51, m | 133.5 | — |
| 38.4 | 1.32-1.62, m | 186.2 | — |
| 72.4 | 3.94, m | 136.5 | 6.88, br d (1.4) |
| 135.2 | 5.53, dd (15.6, 4.5) | 149.8 | — |
| 133.1 | 5.49, dd (15.6, 7.2) | 186.3 | — |
| 40.4 | 2.54, m | 132.9 | — |
| 77.3 | 5.14, br d (9.5) | 127.6 | 8.07, d (8.0) |
| 38.7 | 1.97, m | 133.2 | 7.79, dd (8.0, 1.3) |
| 78.5 | 3.39, br d (9.5) | 14.3 | 0.94, d (7.1) |
| 36.0 | 1.81, m | 16.4 | 2.17, s |
| 79.4 | 3.52, m. |  |  |

2. The method of claim 1, wherein the mammal is human.

3. The method of claim 1, wherein the fungal infection is caused by one or more of *Candida* or *Aspergillus*.

4. The method of claim 1, wherein the fungal infection is caused by one or more of *Candida albicans, Candida glabrata, Candida auris, Aspergillus fumigatus*, and drug-resistant strains thereof.

5. The method of claim 1, wherein a second antifungal other than the compound of Formula I is administered to the mammal in need thereof simultaneously, sequentially or separately with the compound of Formula I, or the pharmaceutical composition.

6. The method of claim 5, wherein the second antifungal is a selected from the group consisting of amphotericin B, flucytosine, fluconazole, micafungin, and forazoline.

7. The method of claim 1, wherein the effective amount of the compound is about 0.01 mg/kg/day to 100 mg/kg/day.

8. The method of claim 1, wherein the effective amount of the compound is about 0.1 mg/kg/day to 5 mg/kg/day.

9. The method of claim 1, wherein the compound is a compound of Formula I.

10. The method of claim 9, wherein the mammal is human.

11. The method of claim 10, wherein the fungal infection is caused by one or more of *Candida* or *Aspergillus*.

12. The method of claim 11, wherein the effective amount of the compound is about 0.01 mg/kg/day to 100 mg/kg/day.

13. The method of claim 1, wherein the compound is a compound of Formula IA.

14. The method of claim 13, wherein the mammal is human.

15. The method of claim 14, wherein the fungal infection is caused by one or more of *Candida* or *Aspergillus*.

16. The method of claim 15, wherein the effective amount of the compound is about 0.01 mg/kg/day to 100 mg/kg/day.

17. The method of claim 1, wherein the compound the compound has the formula, $C_{77}H_{122}O_{26}$ and exhibits one or more of the following spectral features:
one or more $^{13}C$ NMR peaks at or about the ppm chemical shifts in the table below;
one or more $^1H$ NMR peaks at or about the ppm chemical shifts in the table below; or
one or more UV $\lambda_{max}$ at about 204, about 248, about 254, or about 334 nm;

TABLE 2

$^1H$ and $^{13}C$ NMR (MeOH-$d_4$, 500/125 MHz) cyphomycin data

| No. | $\delta_C$ | $\delta_H$, mult. (J in Hz) |
|---|---|---|
| 1 | 168.7 | — |
| 2 | 122.1 | 5.86, br d (15.8) |
| 3 | 153.5 | 7.06, dd (15.8, 6.8) |
| 4 | 43.5 | 2.47, m |
| 5 | 74.2 | 3.78, m |
| 6 | 41.7 | 1.60, m |
|  |  | 1.54, m |
| 7 | 71.8 | 3.78, m |
| 8 | 38.9 | 1.32-1.62, m |
| 9 | 23.0 | 1.45-1.68, m |
| 10 | 38.5 | 1.32-1.62, m |
| 11 | 72.9 | 3.51, m |
| 12 | 36.4 | 1.38-1.47, m |
|  |  | 1.53-1.63 m |
| 13 | 31.9 | 1.69, m |
|  |  | 1.30, m |
| 14 | 36.2 | 2.25, m |
| 15 | 75.8 | 4.69, d (2.2) |
| 16 | 210.6 | — |
| 17 | 99.4 | — |
| 18 | 41.1 | 2.09, m |
|  |  | 1.33, m |
| 19 | 64.9 | 4.08, m |
| 20 | 42.0 | 1.96, m |
|  |  | 1.21, m |
| 21 | 67.7 | 4.20, m |
| 22 | 45.6 | 1.45-1.74, m |
| 23 | 65.4 | 4.08, m |
| 24 | 46.3 | 1.43-1.67, m |
| 25 | 68.2 | 4.04, m |
| 26 | 46.0 | 1.40-1.76, m |
| 27 | 71.3 | 3.79, m |
| 28 | 38.4 | 1.32-1.62, m |
| 29 | 22.7 | 1.51, m |
| 30 | 38.4 | 1.32-1.62, m |
| 31 | 72.4 | 3.94, m |
| 32 | 135.2 | 5.53, dd (15.6, 4.5) |
| 33 | 133.1 | 5.49, dd (15.6, 7.2) |
| 34 | 40.4 | 2.54, m |
| 35 | 77.3 | 5.14, br d (9.5) |

TABLE 2-continued $^1$H and $^{13}$C NMR (MeOH-$d_4$, 500/125 MHz) cyphomycin data

| No. | $\delta_C$ | $\delta_H$, mult. (J in Hz) |
|---|---|---|
| 36 | 38.7 | 1.97, m |
| 37 | 78.5 | 3.39, br d (9.5) |
| 38 | 36.0 | 1.81, m |
| 39 | 79.4 | 3.52, m |
| 40 | 38.5 | 2.00, m |
| 41 | 80.5 | 3.88, m |
| 42 | 22.9 | 1.64, m |
|  |  | 1.36, m |
| 43 | 11.5 | 0.98, t (7.2) |
| 44 | 14.1 | 1.09, d (6.7) |
| 45 | 13.6 | 0.79, d (6.4) |
| 46 | 17.3 | 1.03, d (6.5) |
| 47 | 9.7 | 0.90, d (6.8) |
| 48 | 5.0 | 0.90, d (6.8) |
| 49 | 10.6 | 0.78, d (6.4) |
| 1' | 96.4 | 5.01, br s |
| 2' | 37.9 | 1.93, dd (3.70, 14.0) |
|  |  | 1.55, d (14.0) |
| 3' | 71.2 | — |
| 4' | 81.7 | 3.31, m |
| 5' | 64.7 | 4.44, m |
| 6' | 17.3 | 1.21, d (6.6) |
| 7' | 27.5 | 1.24, s |
| 1" | 104.0 | 4.58, br d (7.6) |
| 2" | 31.3 | 2.01, m |
|  |  | 1.56, m |
| 3" | 28.6 | 2.10, m |
|  |  | 1.56, m |
| 4" | 74.4 | 4.45, m |
| 5" | 74.5 | 3.54, dq (6.1, 9.3) |
| 6" | 18.5 | 1.19, d (6.1) |
| 50 | 175.5 | — |
| 51 | 48.9 | 2.78, dq (8.5, 7.1) |
| 52 | 76.4 | 4.86, d (8.5) |
| 53 | 150.3 | — |
| 54 | 125.3 | 8.01, br s |
| 55 | 133.5 | — |
| 56 | 186.2 | — |
| 57 | 136.5 | 6.88, br d (1.4) |
| 58 | 149.8 | — |
| 59 | 186.3 | — |
| 60 | 132.9 | — |
| 61 | 127.6 | 8.07, d (8.0) |
| 62 | 133.2 | 7.79, dd (8.0, 1.3) |
| 63 | 14.3 | 0.94, d (7.1) |
| 64 | 16.4 | 2.17, s |

18. The method of claim 17, wherein the mammal is human.

19. The method of claim 18, wherein the fungal infection is caused by one or more of *Candida* or *Aspergillus*.

20. The method of claim 19, wherein the compound exhibits $^{13}$C NMR peaks selected from those at about 210.6, about 168.7, about 122.1, about 153.5, about 135.2, about 133.1, about 175.5, about 150.3, about 186.2, and about 186.3 ppm, and/or $^1$H NMR peaks selected from those at about 8.07, about 8.01, about 7.79, about 7.06, about 6.88, about 5.86, about 5.53, about 5.49, about 5.14, about 4.69, and about 3.54 ppm.

\* \* \* \* \*